(12) United States Patent
Lange et al.

(10) Patent No.: US 8,688,387 B2
(45) Date of Patent: Apr. 1, 2014

(54) METHOD FOR THE DETERMINATION OF INTRA- AND INTERMOLECULAR INTERACTIONS IN AQUEOUS SOLUTION

(75) Inventors: Gudrun Lange, Kelkheim (DE); Robert Klein, Frankfurt (DE); Juergen Albrecht, Bad Camberg (DE); Matthias Rarey, Pinneberg (DE); Ingo Reulecke, Hamburg (DE)

(73) Assignees: Bayer CropScience AG, Monheim (DE); Universitaet Hamburg, Hamburg (DE)

( * ) Notice: Subject to any disclaimer, the term of this patent is extended or adjusted under 35 U.S.C. 154(b) by 0 days.

(21) Appl. No.: 13/366,491

(22) Filed: Feb. 6, 2012

(65) Prior Publication Data
US 2012/0202699 A1    Aug. 9, 2012

Related U.S. Application Data

(63) Continuation of application No. 12/446,659, filed as application No. PCT/EP2007/009120 on Oct. 20, 2007, now abandoned.

(30) Foreign Application Priority Data

Oct. 27, 2006 (EP) .................................. 06022487

(51) Int. Cl.
*G01N 33/48* (2006.01)
*G06G 7/58* (2006.01)

(52) U.S. Cl.
USPC ............................................... 702/19; 703/11

(58) Field of Classification Search
USPC ............................................... 702/19; 703/11
See application file for complete search history.

(56) References Cited

FOREIGN PATENT DOCUMENTS

WO    98/54665    12/1998

OTHER PUBLICATIONS

International Search Report for PCT/EP2007/009120 mailed Dec. 14, 2007, two pages.
International Preliminary Report on Patentability for PCT/EP2007/009120 dated Oct. 8, 2008, five pages.
Wernet, et al., "The Structure of the First Coordination Shell in Liquid Water", Science, vol. 304, May 14, 2004, pp. 995-999.

*Primary Examiner* — Michael Borin
(74) *Attorney, Agent, or Firm* — Rankin, Hill & Clark LLP

(57) ABSTRACT

The present invention relates to the determination of intra- or intermolecular interaction between molecules in aqueous solution, the method comprising the steps of: (a) determining the dehydration of all atoms in the intermolecular interface, (b) adding the vacuum hydrogen bond energy, and (c) further adding the change in the free enthalpy of the interacting partners upon their interaction. The obtained results can be used for the prediction if and to what extent two molecules of various origin fit to each other.

17 Claims, 26 Drawing Sheets

| | Contribution derived for ideal functions | Contributions according example 5 | Experimental value |
|---|---|---|---|
| Polar dehydration per H-bond function | $-f_{sat}\varepsilon_{polar...wat} + 1/2\, f_{sat}\varepsilon_{wat...wat}$ = +11 kJ/mol | +4 to +6 kJ/mol | |
| Apolar dehydration | $\varepsilon_{wat...wat}(1-T/373K)$ Corresponds to $-112J/Å^2$ at 298K | $-60$ to $-100 kJ/Å^2$ | $-66 J/Å^2$ (Eisenberg et al, 1986) $-116 J/Å^2$ at 298K (Reynolds et al., 1974) |
| H-bond in vacuum | $\varepsilon^0_{wat...wat}$ = $-20 kJ/mol$ | $-10$ to $-16$ kJ/mol | $-8$ to $-29$ kJ/mol (Jeffrey 1997) |
| Contribution of ideal H-bond in aqueous solution | $f_{unsat}\varepsilon_{wat...wat}$ = $-4 kJ/mol$ | $-2$ to $-5$ kJ/mol | $-2$ to $-6$ kJ/mol (Fersht et al.1985) |
| Contribution of lost H-bond in aqueous solution | $-f_{sat}\varepsilon_{polar...wat} + 1/2\varepsilon_{wat...wat}(1-T/373K)$ = +8.8 kJ/mol | +3 to +4 kJ/mol | +3.3 kJ/mol (Savage et al.1993) +3 to +4 kJ/mol (Lange et al., 2002) |

FIG. 8

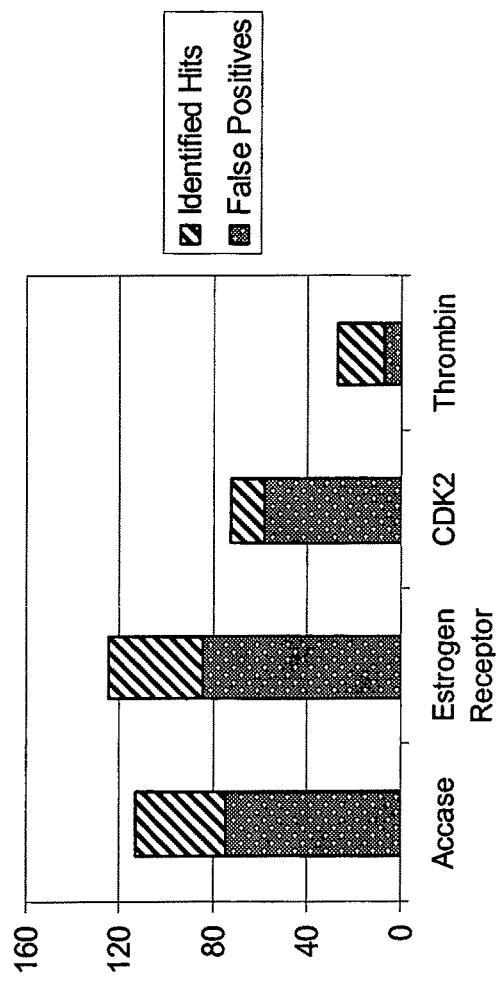
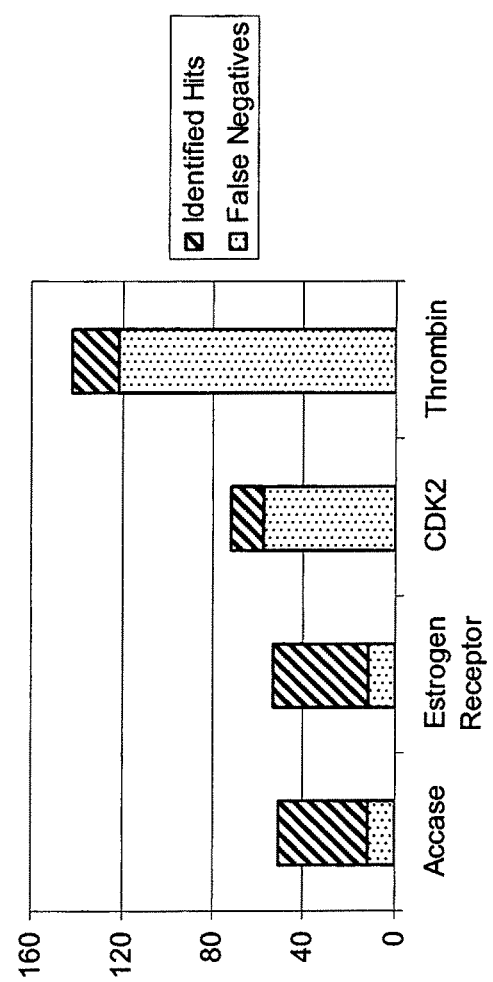
FIG. 11 A
FIG. 11 B

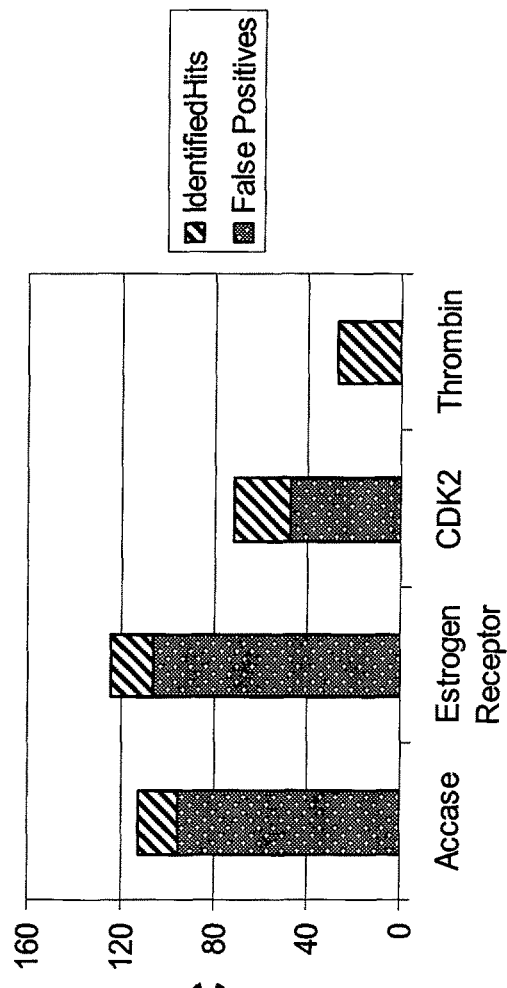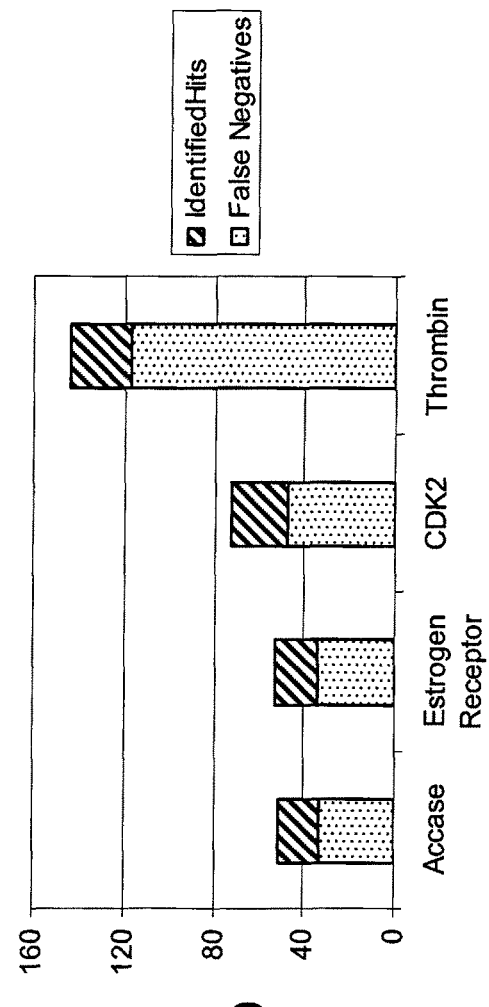
FIG. 11 C
FIG. 11 D

METHOD FOR THE DETERMINATION OF INTRA- AND INTERMOLECULAR INTERACTIONS IN AQUEOUS SOLUTION

The present invention relates to the determination of the interaction between molecules in aqueous solution. The obtained results can be used for the prediction if and to what extent two molecules of various origin fit to each other. This can be used for the identification of agrochemicals and pharmaceuticals.

Over the last few years significant advances have been made in predicting and quantifying the nature of intermolecular interactions in aqueous solution with the use of computer simulations. Although from a purely scientific point of view, these calculations are used for the validations of theories describing the nature of intermolecular interactions, computer simulations find especially useful application in reducing the time required to develop new materials with desirable properties such as pesticides and pharmaceuticals. The closer the theories describing the intermolecular interactions are to reality, the more accurate and helpful will be the calculations. Thus it is of utmost importance to base the calculations on theories which describe the experiments involving intermolecular interactions with sufficient accuracy.

The change in Gibbs free energy ($\Delta G_{bound/unbound}$) due to the formation of an intermolecular interaction such as a ligand binding to a protein has been described as the sum of all individual atomic contribution $\Delta G^{i,j}$) averaged within the statistical ensemble and the changes in the Gibbs free energy of molecule A ($\Delta G^A$) and the molecule B ($\Delta G^B$), respectively (Rarey et al., J. Mol. Biol. 1996, 261: 470-489).

$$\Delta G_{bound/unbound} = \sum_{\substack{i=1 \ldots n \\ j=1 \ldots m}} \Delta G^{i,j} + \Delta G^A + \Delta G^B$$

i=1, ... n: atoms of molecule A in intermolecular interface
j=1, ... m: atoms molecule B in intermolecular interface
$\Delta G^A$: change in the Gibbs free energy of molecule A upon formation of the interface
$\Delta G^B$: change in the Gibbs free energy of molecule B upon formation of the interface Comparison with experiments suggests that the known theories and thus the predictions based on these theories do not describe the interaction between two molecules in aqueous solutions with sufficient accuracy. For instance, the calculated contributions of interfacial H-bonds seem to be often overestimated (Davies and Teague, Angewandte Chemie International Edition 1999, 38: 736-749; Gohlke and Klebe, Angewandte Chemie, International Edition 2002, 41: 2644-2676) and not to be in accordance with the reported experimental values $\Delta G^{i,j}$ between 2.5 kJ/mol (Fersht et al., Nature 1985, 314: 235-8). Selectivity is assumed to be conferred by a network of interfacial H-bonds. However, recently, doubts have been expressed if the selectivity in protein ligand complexes originates from interfacial H-bonds since 'the experimentally obtained contribution of an interfacial H-bond is so small that it cannot give rise to a preferred binding of a specific ligand' (Kool, Annu. Rev. Biomol. Struct. 2001, 30:1-22). Instead it has been proposed that a preferred binding might origin in the favorable contribution of 'hydrophobic interactions' (Davies and Teague, Angewandte Chemie International Edition 1999, 38: 736-749; Kool, Annu. Rev. Biomol. Struct. 2001, 30:1-22) or 'CH•••OR H-bonds' (Klaholz and Moras, Structure 2002, 10: 1197-1204). Thus, the origin of selectivity is still under discussion. The fact that hydrophobic moieties avoid water, the so-called hydrophobic effect, is assumed to be an important contribution to $\Delta G_{bound/unbound}$ (Davies and Teague, Angewandte Chem. International Edition 1999, 38: 736-749). Its origin, however, is still not understood (Abraham et al., J. Am. Chem. Soc. 2002, 124: 7853-56). For instance, it is still widely believed that the hydrophobic effect increases with temperature (Vulevic et al., Biophysical Journal 1997, 72: 1357-75: Chandler, Nature 2005, 437: 640-7) which is against the experience in daily life. Here, it is well known that a phase separation between the greasy and the aqueous phase does take place when the soup becomes cold. Thus it has been so far impossible to calculate the size of the hydrophobic effect based on theoretical assumptions. Instead experimental values extrapolated from partition experiment have been used (Hermann, J. Phys. Chem. 1972, 76: 2754-9; Reynolds et al., Proc. Natl. Acad. Sci. U.S.A. 1974, 71: 2925-7; Eisenberg and MacLachlan, Nature 1986, 319: 199-203; Searle et al., J. Am. Chem. Soc. 1992, 114: 10697-10704).

Most of the available theories used for the scoring of intermolecular interactions assume that the individual atomic interaction types and thus their balance is independent on temperature or additives. Indeed, it has been observed that the change of Gibbs free energy upon the formation of weak intermolecular interactions seems not to be strongly temperature dependent suggesting that an unfavorable enthalpic contribution is compensated by a favorable contribution to entropy (Calderone and Williams, J. Am. Chem. Soc. 2001, 123: 6262-7). It has been suggested that this entropy/enthalpy compensation may be a general thermodynamic requirement resulting from the fact that stronger interactions between molecules will result in a reduction of the configurational freedom of the system and thus a larger reduction of entropy. However, experiments show that this enthalpy/entropy compensation is not found in all systems and thus the general explanation of the origin of the enthalpy/entropy compensation does not hold. In addition, there are several natural processes which show that the individual atomic interaction types and in particular their balance is dependent on the temperature. For instance, entropy driven self-association processes lead to well defined supramolecular structures upon temperature increase (for review see for instance Oosawa and Asakura, Thermodynamics of the Polymerization of Protein 1976, Publisher: Academic, London). There is no molecular explanation for these processes and different authors attribute this behavior to either the increase in H-bonding (Leikin et al., Structural Biology 1995, 2: 205-210) or to the presumed increase of the hydrophobic effect at higher temperatures (Vulevic et al., Biophysical Journal 1997, 72: 1357-75). Similarly, the driving force for the folding and unfolding of proteins as a function of temperature or induced by organic solvents is still under discussion.

It is well known that the required change in $\Delta G_{bound/unbound}$ for an x-fold increased affinity can be calculated using the expression $\Delta G_{bound/unbound} = -RT \ln K$. For instance, a 1000 fold increased affinity corresponds to a change in $\Delta G_{bound/unbound}$ of 17 kJ/mol at room temperature. Comparing the size of the observed $\Delta G_{bound/unbound}$ with the size of the individual contributions $\Delta G^{i,j}$ attributed to intermolecular interactions such as the formation of an interfacial H-bond or the burial of an apolar surface, it becomes obvious that in addition to stabilizing contributions $\Delta G^{i,j}$, there must exist a fair amount of counterbalancing destabilizing contributions $\Delta G^{i,j}$ to $\Delta G_{bound/unbound}$. In particular, significant destabilizing contributions to $\Delta G_{bound/unbound}$ have to be present in natural processes since low affinity binding is required in order to have a dynamic equilibrium. Indeed, it has been reported for protein structures that stabilizing contributions to $\Delta G_{fold/unfold}$ mainly due to the hydrophobic effect are counterbalanced by destabilizing contributions, the so called 'lost H-bonds' (Savage et al., J. Chem. Soc. Faraday Trans. 1993, 89: 2609-17). The exact physical origin of these destabilizing contributions is still unknown. Thus, most scoring functions account for them not directly. Instead, mathematical filters have been used in order to reject unwanted intermolecular interaction types such as an H-bond function pointing into a hydrophobic pocket (Stahl and Bohm, J. Mol. Graphics & Modeling 1998, 16: 121-132). However, the presence of these interaction types in experimental complex structures indicate that they are under certain conditions allowed and deselecting compounds with these features may result in a significant number of false negatives.

These experimental findings suggest that the available theories and thus the predictions based on these theories do not describe the interactions between two molecules in aqueous solution accurately enough. It has always been suspected that the reason for this lies within the water and the insufficient description of water and its interaction with functional groups. The experimental structures of the different ice polymorphs have shown that the water molecules form in ice a regular 3D structure in which all four H-bonds per water are made with ideal geometrical parameter. However, in liquid water, there is only a low range order present. As seen in the pair correlation functions calculated from wide-angle neutron and x-ray scattering data, there is a wide and temperature dependent distribution of distances between individual water molecules in bulk water indicating that not all H-bonds are made and/or have ideal geometry at a given time. The water molecules form a network connected by transient H-bonds in which individual H-bonds are continuously made and broken. Accordingly, there is a perpetual change of the H-bond network formed by the water molecules even though the number of made and broken H-bonds remains constant in the course of time. However, as seen in high resolution neutron structures of water in clathrates, water still has a remarkable preference for H-bonds with HOW•••O distances close to 1.8 Å and angles between 160 and 180° and tetrahedral H-bonded arrangements seem still to be strongly preferred structural elements in water, however transient they may be. The view that not all H-bonds are made within bulk water, was first proposed by Pauling (The Nature of the Chemical Bond and the Structure of Molecules and Crystals. An Introduction to Modern Structural Chemistry. 3rd ed., 1960, Publisher: Cornell University Press, Ithaca, N.Y). He calculated the fraction of broken H-bonds at 273K from the ratio of the enthalpies of fusion and evaporation. The resulting value of 15% broken H-bonds at 273K is still widely accepted (see for instance Lee and Graziano, J. Am. Chem. Soc. 1996, 118: 5163-5168). No influence of the temperature upon the fraction of made H-bonds in the water network was given. Experiments confirm the presence of broken H-bonds and show that increasing the temperature of bulk water results in an increase of broken H-bonds within the water network. However, the predicted values calculated according to Pauling do not agree with the experimental data obtained using experimental techniques such as neutron diffraction (Soper et al., Chemical Physics 2000, 258: 121-137).

The exact calculation of the entropy of bulk water has not been possible so far since the water network does not consist of independent molecules which can be treated using for instance Boltzmann statistics. Nevertheless, this is widely assumed and done in the literature (see for instance Klebe and Böhm, Journal of receptor and signal transduction research 1997, 17: 459-73 or Kellog et al., J. Comp.-Aided Mol. Des. 2001, 15: 381-393). A simple theoretical approach to estimate the entropy of water has been based on the H-bond counting theory whereby the number of H-bonded neighbors is related to the probability for the various donor/acceptor sites of any water molecule to belong to a molecular water association (Luzar, Chemical Physics Letter 1983, 96: 485-90; Veytsman, J. Phys. Chem. 1990, 94: 8499). This method has given the same expressions relating the fraction of made H-bonds to the entropy of the water network than a completely different thermodynamic perturbation theory based on cluster diagrams (Wertheim, J. Chem. Phys. 1987, 87: 7323-31). Broken H-bonds occur not only with increasing temperature in bulk water but also at surfaces such as the water/air surface. Luzar (Chemical Physics Letter 1983, 96: 485-90) has calculated that the number of possible H-bonds is reduced by 25% in a surface layer of thickness d=3 Å based on a simple geometrical model.

Individual functional groups differ in the way they interact with the water network. In particular, the nature of the hydrophobic effect has been extensively investigated but is still not fully understood. In particular, the driving force which causes hydrophobic moieties to avoid water and instead to form aggregates, remains elusive. Often, the emphasis was more on the aggregation of hydrophobic groups and in fact it was found that the size of the hydrophobic effect seems to correlate well with the size of the hydrophobic surface area which is buried. However, no attractive force could be identified which explains the attraction of these moieties. The van-der-Waals interactions are not specific to hydrophobic atoms and too small to explain the magnitude of the hydrophobic effect. Alternatively, the hydrophobic effect can be analyzed by looking at the H-bonds within the water network around hydrophobic moieties (Silverstein, J. Am. Chem. Soc. 2000, 122: 8037-41). Various theories based on Paulings calculation have been put forward involving made and broken water H-bonds around hydrophobic moieties. They are still fiercely disputed and seem not to describe the phenomenon 'hydrophobic effect' satisfactorily (Abraham et al., J. Am. Chem. Soc. 2002, 124: 7853-56). Recent neutron scattering experiments have confirmed that water retains its tetrahedral structure and forms an H-bonded network in solutions. However, there seems to be a pronounced difference between the water structure around polar and apolar atoms. The separated pair correlation functions derived from empirical potential structure refinement of neutron scattering data (Soper et al., J. Phys. Chem. 1996, 100: 1357-67) show that the water around the DMSO (Dimethylsulfoxid) oxygen is strongly H-bonded and that the geometry of the made H-bonds between the DMSO oxygen and the water network is very similar to that found between individual water molecules in pure water. In contrast to this polar function, the angular distribution has only an insignificant maximum suggesting that there is only a very weak orientation of the water molecules due to their interaction with the methyl group. In summary, it is not understood how the strength of the interaction between a functional group and the water network influences the Gibbs free energy which is needed to remove (dehydrate) the functional group from the water network or integrate (hydrate) it into the water network.

There is a general agreement that better scoring functions are needed for docking and virtual screening (Warren et al., J. Med. Chem. 2006, 49:5912:31). Several attempts were made to modify terms describing individual interactions and consensus functions integrating various scoring functions were used with limited success (Clark et al., J. Molec. Graphics & Modeling 2002, 2: 281-295). Knowledge-based scoring functions were introduced in order to base the scoring more on experimental observed protein ligand interactions. Typical distances between interacting groups were extracted from high quality x-ray structures and formed the experimental foundation for a radial distribution function describing the likelihood that a particular protein ligand interaction is found (Velec et al., J. Med. Chem. 2005, 48: 6296-6303). A force field based on log $P_{o/w}$ has been derived in order to include the dehydration into the scoring empirically. An interaction propensity based on its partial Log $P_{o/w}$ is assigned to each atom in a molecule. Using an empirical mathematical function, the score between two interacting atoms is calculated resulting in either stabilizing (hydrophobic hydrophobic interaction or acid-base interaction) or destabilizing contributions to the Gibbs free energy (Kellog et al., J. Comp.-Aided Mol. Des. 2001, 15: 381-393). However, all published attempts have not lead to a significantly improved scoring function. The underlying reason for this lies in the imperfect description of water and its interaction with functional groups. Therefore, there was a need to find an improved description of water and its interaction with functional groups in order to determine the interaction between two molecules in aqueous solution with a higher reliability.

We set out to investigate the peculiarities of water, how they influence the interaction of different functional groups with water and thus give rise to the unexpected contributions $\Delta G^{ij}$ to $\Delta G_{bound/unbound}$. The above problem was solved by developing a method to incorporate these findings in the scoring of intermolecular interactions in aqueous solution. The water network represents the statistical ensemble which will be analyzed. A new determination of the made and broken H-bonds within the water network based on a thermodynamic cycle results in significantly different values for the fraction of made and broken H-bonds than those currently available. In addition, instead of considering the transient network interconnections i.e. the made and unmade H-bonds, we shift the emphasis to the network nodes i.e. the satisfied or unsatisfied water H-bond functions of the water molecules. Though in pure water the fraction of made/broken H-bonds is identical to the fraction of satisfied/unsatisfied H-bonds functions, there is a crucial difference in the presence of solutes or at surfaces. Neither the presence of unsatisfied H-bond functions nor the balance between satisfied and unsatisfied H-bond functions within the water network is considered in the available theories describing the interaction of molecules with water. Introducing the new physical units 'fraction of satisfied water H-bond functions ($f_{sat}$)' and 'fraction of unsatisfied water H-bond functions ($f_{unsat}$)' into the description of water and its interaction with functional groups, brings the predictions significantly better in agreement with the corresponding experiments.

The present invention relates to a method for the determination of intra- or intermolecular interactions in an aqueous solution, said method comprising the steps of:
(a) determining the dehydration ($\Delta G_{dehydration}$) of all atoms in the intermolecular interface,
(b) adding the vacuum hydrogen bond energy ($\epsilon_H$-bond), and
(c) further adding the change in the free enthalpy of the interacting partners upon their interaction.

In a preferred embodiment the present invention relates to a method for the determination of intra- or intermolecular interactions in an aqueous solution, said method consisting of:
(a) determining the dehydration ($\Delta G_{dehydration}$) of all atoms in the intermolecular interface,
(b) adding the vacuum hydrogen bond energy ($\epsilon_H$-bond), and
(c) further adding the change in the free enthalpy of the interacting partners upon their interaction.

The present invention particularly relates to a method, wherein the dehydration is quantified by:
(a) the determined fraction of saturated H-bond functions within the water network ($f_{sat}$),
(b) the determined fraction of unsaturated H-bond functions within the water network ($f_{unsat}$),
(c) the determined hydrogen bond energies between water molecules in the water network ($\epsilon^\circ_{wat\ldots wat}$), and
(d) in case of a polar function the determined hydrogen bond energy between the polar function and the water network ($\epsilon^\circ_{pol\ldots wat}$).

The present invention more particularly relates to a method, wherein $f_{sat}$ and $f_{unsat}$ are defined in pure bulk water by the terms as listed under (a) and (b) of the before $$f_{sat}(T)=(\Delta H_{Fusion}+c_p(T-273K)/(\Delta H_{Fusion}+\Delta H_{Evaporation}+c_p*(373K-273K)), \text{ and} \quad (a)$$

$$f_{unsat}(T)=(\Delta H_{Evaporation}+c_p*(373K-T)/(\Delta H_{Fusion}+\Delta H_{Evaporation}+C_p*(373K-273K)), \quad (b)$$

under the prerequisite that $f_{sat}+f_{unsat}=1$, and wherein
(i) $\Delta H_{Fusion}$ means the Enthalpy of the fusion of ice;
(ii) $\Delta H_{Evaporation}$ means the Enthalpy of Evaporation of water; and
(iii) $c_p$ means specific heat of water.

The invention preferably relates to a method, wherein in case of polar functions a relationship between the dehydration term and the hydrogen bond energy ($\epsilon^\circ_{pol\ldots wat}$) involving $f_{sat}$ is used.

Further, the invention preferably relates to a method, wherein in case of polar functions the relationship $$\Delta G_{dehydration}^{i} \sim f_{sat}^{i} \epsilon^{i\ldots wat}$$

is valid.

Preferably, the invention relates to a method, wherein $f_{sat}$ is within a range 0.75 to 0.90, more preferably $f_{sat}$ is within a range 0.82 to 0.88, most preferably $f_{sat}$ is within a range of 0.84 to 0.87.

The invention also relates to the use of a method for the determination of intra- or intermolecular interactions in an aqueous solution, said method comprising the steps of:
(a) determining the dehydration ($\Delta G_{dehydration}$) of all atoms in the intermolecular interface,
(b) adding the vacuum hydrogen bond energy ($\epsilon_H$-bond), and
(c) further adding the change in the free enthalpy of the interacting partners upon their interaction for the calculation of molecular interactions between at least 2 molecules in an aqueous solution and wherein one of the molecules is a target molecule which is to be bound by at least one interacting molecule, particularly in which the target molecule is selected from the group consisting of proteins, nucleic acid molecules, or lipids, more particularly in which the target molecule is selected from the group consisting of cell wall proteins, membrane bound proteins, water soluble proteins, cellular proteins, enzymatic proteins, regulatory proteins, ion channel proteins, carrier proteins, aquaporins, vacuolar proteins, golgi apparatus proteins, cytoskeleton proteins, DNA- or RNA-replication proteins, DNA- or RNA-recombination proteins, viral proteins, mitochondrial proteins, plastid proteins involved in the respiration and photorespiration apparatus, proteins belonging to the signal transduction pathway, receptors, G-proteins, senescence proteins, plant stress proteins (including abiotic and biotic plant stress proteins), HMG-proteins (high mobility group proteins), LMG-proteins (low mobility group proteins), Terpenoid synthesis proteins, DNA-molecules, RNA-molecules, transcriptions factors, phospholipids, galactosylglycerides, glucocerebrosides, and sterols, and in which the interacting molecule is selected from the group consisting of proteins, enzyme inhibitors, agonist, antagonists, small weight compounds (molecular weight<600 g/mol) and fragments of the latter.

The invention also relates to the use of a method for the determination of intra- or intermolecular interactions in an aqueous solution, said method comprising the steps of:
(a) determining the dehydration ($\Delta G_{dehydration}$) of all atoms in the intermolecular interface,
(b) adding the vacuum hydrogen bond energy ($\epsilon_H$-bond), and
(c) further adding the change in the free enthalpy of the interacting partners upon their interaction
for the calculation of molecular interactions between at least 2 molecules in an aqueous solution and wherein one of the molecules is a target molecule which is to be bound by at least one interacting molecule in order to
(a) fulfill a virtual screening analysis of compound libraries
(b) identify of at least one interacting molecule with affinity to its specific target molecule, (c) identify and visualize the interacting portions of the target molecule and its interacting molecule thereby enabling the estimation and/or definition of the correct binding mode, (d) identify interacting parts of the target molecule and its interacting molecule thereby enabling the prediction of the strength of the binding of the interacting to its target molecule, and (e) identify the interacting parts of the target molecule and its interacting molecule and thereby enabling the identification of regions contributing either favorably or unfavorably to the binding of the interacting molecules to the specific target molecule.

The invention also relates to the use of a method for the determination of intra- or intermolecular interactions in an aqueous solution, said method comprising the steps of:
(a) determining the dehydration ($\Delta G_{dehydration}$) of all atoms in the intermolecular interface,
(b) adding the vacuum hydrogen bond energy ($\epsilon_H$-bond), and
(c) further adding the change in the free enthalpy of the interacting partners upon their interaction
and in which the interface between the target molecule and its interacting molecule is defined by three-dimensional coordinates that are:
(a) defined by experimental data obtained from protein crystallography methods, X-ray diffraction, or NMR, or
(b) obtained from computer based calculations, particularly by applying the means of docking, molecular dynamics (MD) or Monte Carlo (MC) simulations, or
(c) obtained by manual maneuvering of the interacting molecule inside its primary docking area of the target molecule.

BRIEF DESCRIPTION OF THE FIGURES

FIG. 2 B shows the difference in enthalpy ($\Delta H$, squares), entropy term ($-\Delta TS$, triangles) and Gibbs free energy ($\Delta G$, crosses) between water at temperature T and water at 373K as a function of temperature T. $\Delta H$, $-\Delta TS$ and $\Delta G$ between water at T=298K and 373K are indicated by an arrow.

FIG. 3 B shows $\Delta H$ (squares), $-T\Delta S$ (triangles) and $\Delta G$ (stars) in kJ/mol for generating an additional unsatisfied H-bond function in the water network as a function of the temperature T. The values for $\Delta H$, $-T\Delta S$ and $\Delta G$ at 298K are indicated by arrows.

FIG. 3 C shows $f_{unsat}$ (triangles) and the term characterizing the lack of enthalpy/entropy term compensation (1−T/373) (squares) as a function of the temperature in the water network. The dotted line marks the temperature T=312K in pure water at which both correction terms intersect each other.

FIG. 8 shows a comparison between the contributions predicted for 'ideal functional' groups according to examples 1-3, the values extracted according to example 5 and the respective published experimental data.

FIG. 9 B shows the calculated contributions to $\Delta G_{bound/unbound}$ of individual ligand atoms in the protein ligand interface of the estrogen receptor and modified raloxifene.

FIG. 9 C shows the calculated contributions to $\Delta G_{bound/unbound}$ of individual ligand atoms in the protein ligand interface of the SH2 domain of src and Ru79181 (J. Med. Chem. 2002 45: 2915-22). The ligand atoms O28 and N19 are marked.

FIG. 10 B shows the enrichment calculations for the estrogen receptor. The enrichment is shown for the following scoring functions: FlexX2.0, HYDE, ChemScore, G-Score, PMF-Score and ScreenScore.

FIG. 10 C shows the enrichment calculations for CDK2. The enrichment is shown for the following scoring functions: FlexX2.0, HYDE, ChemScore, G-Score, PMF-Score and ScreenScore.

FIG. 10 D shows the enrichment calculations for thrombin. The enrichment is shown for the following scoring functions: FlexX2.0, HYDE, ChemScore, G-Score, PMF-Score and ScreenScore.

FIG. 13 B shows the stabilizing versus the destabilizing contributions for the crystal structure (triangle) and the docking solutions (crosses). It becomes obvious that only the crystal structure has considerable more stabilizing than destabilizing contributions and none of the docked poses will be observed in experiments The average fraction of satisfied/unsatisfied H-bond functions within the water network can be estimated assuming that the sum of (a) enthalpy of fusion ($\Delta H_{Fusion}$=6 kJ/mol), (b) the enthalpy of heating water from 273 to 373K ($\Delta H_{273-373K}$) and (c) enthalpy of evaporation ($\Delta H_{Evaporation}$=40.7 kJ/mol) is the energy needed to break all H-bonds in ice and transfer the water molecules to the vapor state. The corresponding thermodynamic cycle is shown in FIG. 1A. Since the specific heat of water is constant between 273 and 373K, the enthalpy for heating water can be calculated from the specific heat (cp=0.075 kJ/molgrad) and is $\Delta H_{273-373K}$=7.5 kJ/mol. Thus, the total energy needed to break the four H-bonds in ice and transfer water into the vapor state is 54.18 kJ/mol. The fraction of satisfied and unsatisfied H-bond functions in the water network can be calculated as follows:

$$f_{sat}(T)=(\Delta H_{Fusion}+c_p(T-273K)/(\Delta H_{Fusion}+\Delta H_{Evaporation}+c_p(373K-273))$$

$$f_{unsat}(T)=(\Delta H_{Evaporation}+c_p(373K-T)/(\Delta H_{Fusion}+\Delta H_{Evaporation}+c_p(373K-273))$$

$$\text{and } f_{sat}(T)+f_{unsat}(T)=1$$

Figure 1A:
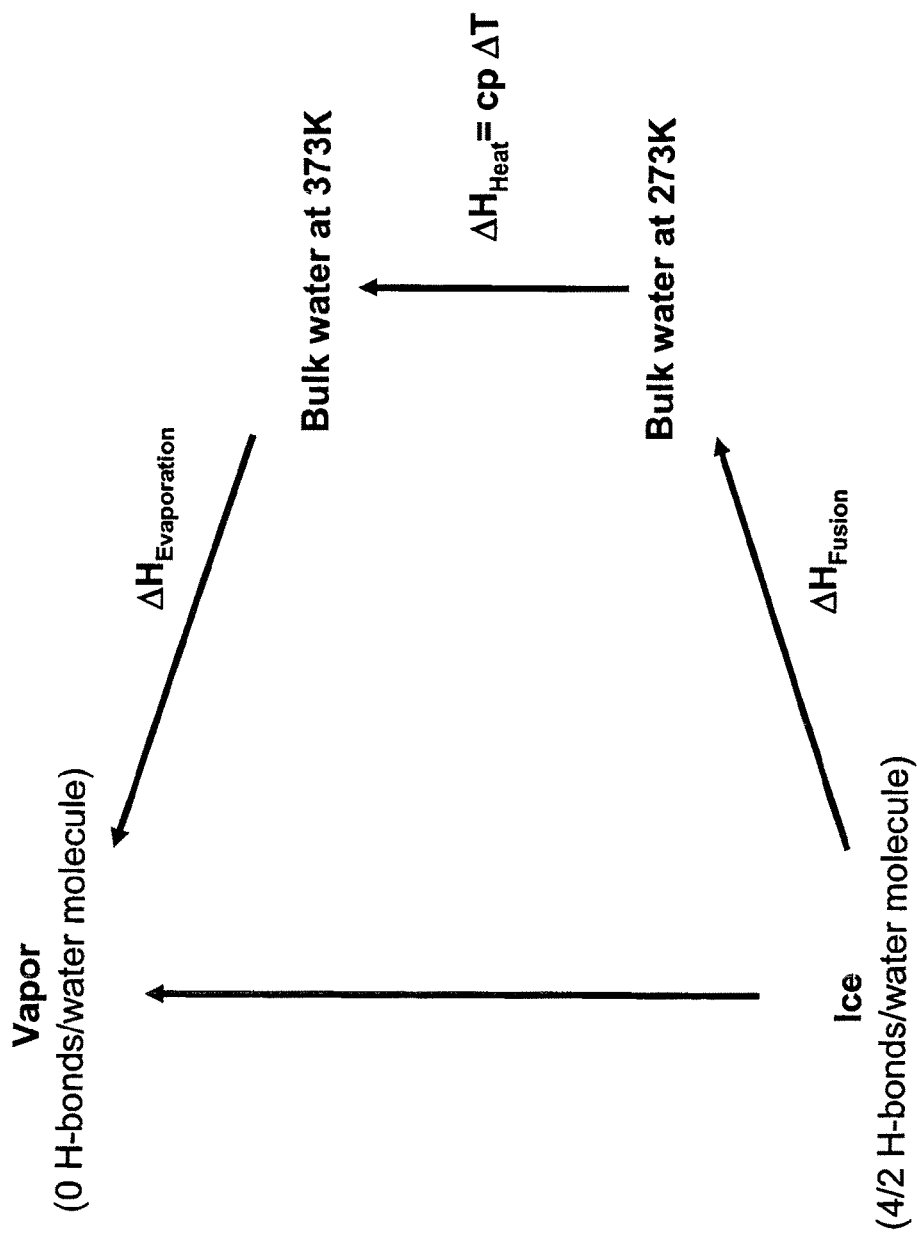
FIG. 1A shows the thermodynamic cycle which is used to calculate $f_{sat}$ and $f_{unsat}$.
Figure 1B:
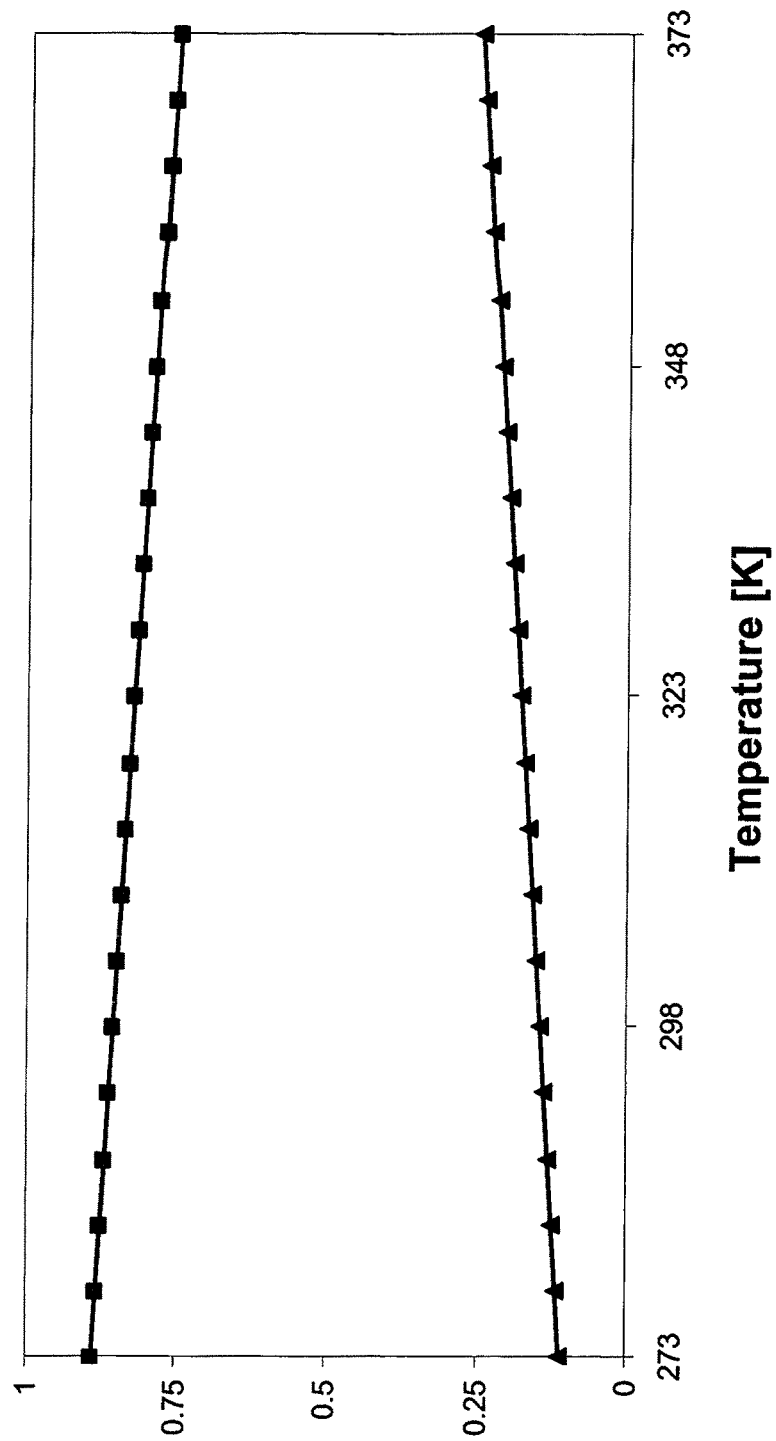
FIG. 1B shows $f_{sat}$ (squares) and $f_{unsat}$ (triangles) as a function of temperature.

FIG. 1B shows the fraction of satisfied and unsatisfied H-bond functions within the water network. In the water network at 273K, already 11% of the H-bond functions are unsatisfied since the enthalpy of fusion represents 6 kJ/mol of the total 54.18 kJ/mol. In a living organism at 313K the percentage of unsatisfied H-bond functions has increased to roughly 17% while at the boiling point (373K) 25% of the H-bond functions are unsatisfied in the water network. This means that the interface between liquid water and vapor is characterized by water molecules which have in average one unsatisfied and three satisfied H-bond functions. A further reduction of satisfied H-bond functions within the water network to an average value below three satisfied H-bond functions per water molecule causes a breakdown of the three-dimensional water network and liquid water is evaporating. This can be rationalized since three linear independent vectors, i.e. three directed H-bonds are needed to span a three-dimensional space. The calculated fraction of unsatisfied H-bond functions at the liquid/vapor interface at 373K is identical to the fraction of made/broken H-bonds which had been estimated for surfaces (Luzar, Chemical Physics Letter 1983, 96: 485-90; Wernet, Science 2004, 304: 995-999). In contrast to the currently accepted figure for the fraction of broken H-bonds in the literature (Pauling, The Nature of the Chemical Bond and the Structure of Molecules and Crystals. An Introduction to Modern Structural Chemistry. 3rd ed., 1960, Publisher: Cornell University Press, Ithaca, N.Y), our estimated values agree well with the published fractions of made/broken H-bonds which were determined using experimental techniques such as neutron diffraction (Soper et al., Chemical Physics 2000, 258: 121-137) and X-ray absorption spectroscopy (Wernet, Science 2004, 304: 995-999).

The H-bond energy between two water H-bond functions can be calculated by dividing the total enthalpy for breaking the four H-bonds per water molecules by two, i.e. $\epsilon_0^{wat\cdots wat}$=54.18/2 kJ/mol=27.1 kJ/mol. Even though, each individual water molecule in ice makes four H-bonds, the equivalent of only two H-bond energies have to be assigned to each water molecule in order to avoid double counting. This value is within the range reported using experimental methods. The potential of a directed interaction such as an H-bond has distinct minima for certain distances and angles. As a result, the interacting atoms are orientated towards each other with a well defined geometry. The H-bond energy $\epsilon_0$ is only realized at the ideal geometry while deviations from the ideal distance between donor X—H and acceptor Y or from the ideal angle X—H•••Y forced upon the system by external constraints give rise to a weaker interaction energy $\epsilon$ with $\epsilon < \epsilon_o$. $F_{sat}(T)$ seems to give a temperature dependent estimate on how much the average H-bond within the water network is weakened due to the temperature dependent deviation from ideal geometry within the network. Thus within the statistical ensemble $\epsilon^{wat \ldots wat} = f_{sat}(T) \epsilon_0^{wat \ldots wat}$. Since the statistical ensemble consists of the whole transient network, the statistical average is the same if at one extreme the fraction $f_{sat}$ is considered locally as being ideally made and other H-bonds within the water network not at all or if at the other extreme they are all made with the same lower quality. It should be pointed out, that assigning H-bond energies to individual water molecules or looking at clusters of a limited size instead of looking at the whole statistical ensemble gives rise to serious discrepancies with the experimental data as has been experienced by Wernet et al. (Science 2004, 304: 995-999).

Since between 89% at 273K and 75% at 373K of H-bond functions participate in the water network, the molecular weight and number average of the water network is extremely high. In contrast to non interacting particles such as found in the ideal gas, the entropy of networks is not linearly dependent on the number of molecules or clusters forming the network. Instead, the number of accessible states in networks is directly correlated to network errors (Flory, Principles of Polymer Chemistry 1953, Publisher: Cornell Univ. Press, Ithaca, N.Y). In our view, the unsatisfied H-bond functions in the water network represent the network errors. Similarly to an increased number of chain ends in polymer gels, a higher number of unsatisfied H-bond functions in the water network gives rise to a larger number of accessible states and thus to a larger entropy. Thus, $f_{unsat}(T)$ gives an estimate of the entropy term contribution ($-T\Delta S$) in the water network due to the presence of the H-bonds.

From the three-dimensional structure of the water network follows that a decrease of enthalpy i.e. breaking of H-bonds is accompanied by an increase in entropy i.e. an increase in the number of realizable states for the water H-bond network. The water network is at any temperature in a dynamic equilibrium which is characterized by a specific but temperature dependent fraction of satisfied/unsatisfied H-bond functions within the water network. In the equilibrium, the Gibbs free energy is in its minimum and $\Delta G = \Delta H - T\Delta S$ has to be zero for any change within the water network such as breaking or making H-bonds. Breaking H-bonds within a network is an endothermic process ($\Delta H < 0$) while at the same time the entropy term, the product of the temperature with entropy, increases ($T\Delta S > 0$). Making H-bonds is an exothermic process ($\Delta H > 0$) while at the same time the entropy term decreases ($T\Delta S < 0$). The questions arises if $\Delta H$ is compensated by the corresponding term for $T\Delta S$ for each broken or made water H-bond, respectively, or if $\Delta G = 0$ can only be maintained if in a two step process for each additionally made water H-bond another water H-bond is broken. Assuming that $\Delta H$ is not compensated by the corresponding entropy term $T\Delta S$ ($\Delta H \neq T\Delta S$) the making of a single network H-bond results in $\Delta G \neq 0$. At any fixed temperature, this non-zero Gibbs free energy change can be compensated by breaking an H-bond elsewhere in the water network which keeps the system in equilibrium and $f_{sat}/f_{unsat}$ constant. However, comparing the water network at different temperatures, the assumption that the change in enthalpy due to the making/breaking of H-bonds is not compensated by a corresponding change in the entropy term gives rise to severe inconsistencies since the ratio of $f_{sat}/f_{unsat}$ changes with the temperature and/or in the presence of surfaces. Therefore we propose that only if the enthalpy change is compensated by the corresponding change in the entropy term, the water network stays in the equilibrium at any temperature and during any processes including processes which lead to a change in $f_{sat}$ and $f_{unsat}$ (enthalpy/entropy term compensation of water).

Figure 2:
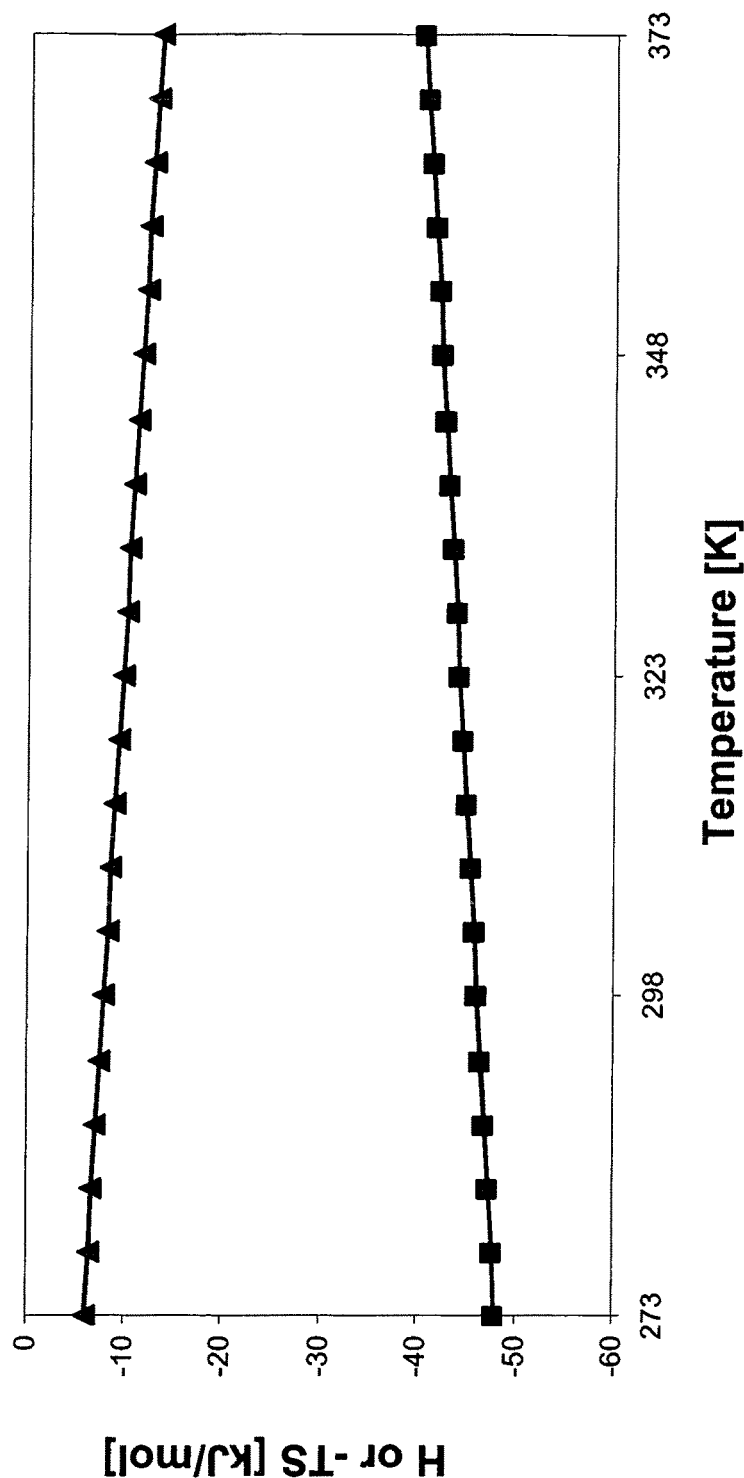
FIG. 2 A shows the average enthalpy H (squares) and entropy term −TS contribution (triangles) of the four H-bond functions per water molecule towards the Gibbs free energy of the water network as a function of the temperature.
Figure 2B:
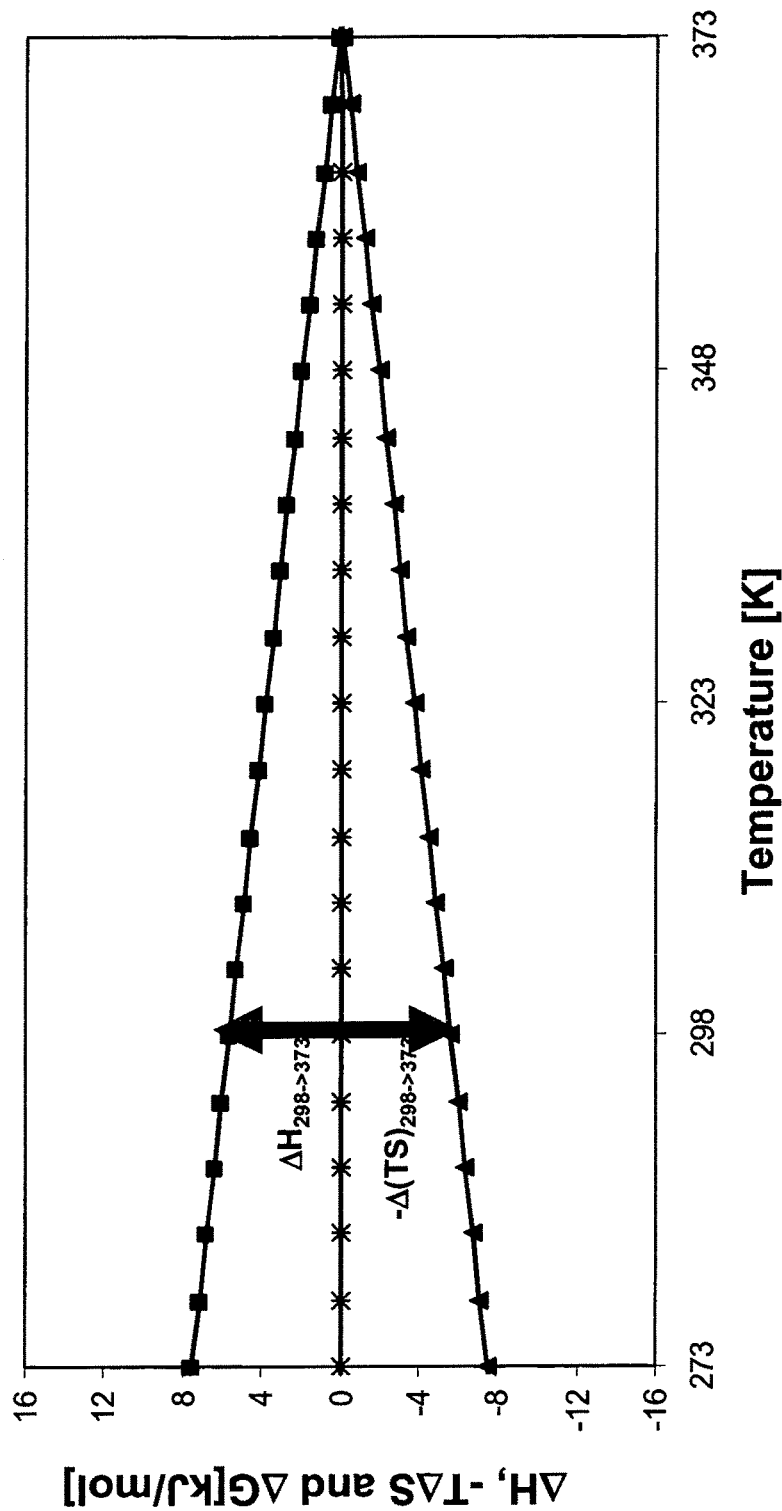

By breaking or making H-bonds within its network, the contribution of the H-bonds to the Gibbs free energy of the water network is shifted between enthalpy and entropy term thereby allowing the water network to adapt to changes in external parameters such as temperature or the presence of surfaces. This enthalpy/entropy term compensation within the water network is possible up to a lower limit of three satisfied H-bond functions per average water molecule i.e. $f_{sat} = 0.75$ and $f_{unsat} = 0.25$. Further reduction of $f_{sat}$ within the water network results in a break-down of the three-dimensional water network and phase separation takes place. Thus the statistically fourth H-bond which an individual water molecule can make is not essential in order to maintain the liquid structure of bulk water. Its H-bond energy $\epsilon^0_{wat \ldots wat}$ is in any case −27.1 kJ/mol. However, depending on external conditions, it contributes differently to the Gibbs free energy of the water network: a pure enthalpy contribution if all statistically fourth H-bond function are fully satisfied i.e. in ice ($f_{unsat} = 0$, $f_{sat} = 1$) or a pure entropy term contribution if the statistically fourth H-bond functions are unsatisfied i.e. at 373K in bulk water or at surfaces ($f_{unsat}(T) = 0.25$ and $f_{sat}(T) = 0.75$). There is a mixed entropy and enthalpy contribution in bulk water between 273K and 373K since some of the statistically $4^{th}$ H-bonds are satisfied and some unsatisfied ($0.11 < f_{unsat} < 0.25$ and $0.89 > f_{sat} > 0.75$). FIG. 2A shows the enthalpy and entropy term contribution of the four H-bonds per water molecule towards the Gibbs free energy of the water network as a function of the temperature. The enthalpy contribution corresponds to the fraction of satisfied water H-bond functions i.e. $H(T) = f_{sat}(T) \cdot 2\epsilon_0^{wat \ldots wat}$, while the contribution of the entropy term corresponds to the fraction of unsatisfied water H-bonds i.e. $-TS(T) = f_{unsat}(T) 2\epsilon_0^{wat \ldots wat}$. The enthalpy/entropy term compensation within the water network can be seen when comparing water at temperature T with water at 373K. FIG. 2B shows the difference in enthalpy ($\Delta H$), Gibbs free energy ($\Delta G$) and entropy term ($-\Delta\Delta S$)) between the water network at temperature T and water at 373K for different temperatures T.

$$\Delta H = H(T = 373 \text{ K}) - H(T)$$
$$= +(0.75 - f_{sat}(T)) \cdot 2\varepsilon_0^{wat \ldots wat} > 0$$
$$-\Delta(TS) = 373 \text{ K} \cdot S(T = 373 \text{ K}) - TS(T))$$
$$= +(0.25 - f_{unsat}(T)) \cdot 2\varepsilon_0^{wat \ldots wat}$$
$$= -(0.75 - f_{sat}(T)) \cdot 2\varepsilon_0^{wat \ldots wat} < 0$$

This shows that the change in the water network enthalpy due to an increase in temperature from T to T=373K is compensated by the associated change in the entropy term of the water network.

The presence of the physical values $f_{sat}$ and $f_{unsat}$ has an highly unexpected impact on the desolvation of functional groups in aqueous solution. We propose that the different behavior of functional groups is related to how the H-bond energy between the corresponding functional group and the water network compares with the H-bond energy between individual water molecules. The two extreme cases will be discussed here (a) $\epsilon_0^{function \ldots wat} \approx \epsilon_0^{wat \ldots wat}$, (b) $\epsilon_0^{function \ldots wat} \approx 0$.

Functions which have roughly the same H-bond energy to water than water H-bonds, i.e. $\epsilon_0^{function \ldots wat} \approx \epsilon_0^{wat \ldots wat}$, integrate fully into the water network and can be treated similar to water molecules. These functions will be referred to here as polar functions and include uncharged oxygen and nitrogen H-bond donors and acceptors. The presence of a polar function does not change $f_{sat}/f_{unsat}$ within the water network and does not disturb the enthalpy/entropy term compensation of bulk water. Similar to H-bonds between water molecules, the statistical average H-bond energy $\epsilon_0^{polar \ldots wat}$ for making and breaking an H-bond between a polar function and the water network is weakened by the presence of the unsatisfied H-bond functions in the water network. The enthalpy loss is off-set by the enthalpy gain due to the re-integration of the released water H-bond function into the water network. For each dehydrated polar function one water H-bond function is released and two released H-bond functions give rise to an additional water H-bond contributing to the Gibbs free energy of the water network. Thus $\Delta G_{dehydration}$ and $\Delta G_{hydration}$ for a polar function can be calculated as:

$$\Delta G_{dehydration}^{polar} = -f_{sat} \cdot \epsilon^{polar \ldots wat} + \tfrac{1}{2} f_{sat} \cdot \epsilon_0^{wat \ldots wat}$$

$$\Delta G_{hydration}^{polar} = +f_{sat} \cdot \epsilon^{polar \ldots wat} - \tfrac{1}{2} f_{sat} \cdot \epsilon_0^{wat \ldots wat}$$

The H-bond energy $\epsilon^{polar \ldots wat}$ as a function of the distance and angle can be calculated using various methods and has its maximal value $\epsilon_0$ only at ideal geometry. FIG. 3A shows $\Delta G_{dehydration}^{polar}$ for a polar function as function of temperature assuming that $\epsilon^{polar \ldots wat}$ equals 27.1, 20, or 15 kJ/mol, respectively. $\Delta G_{dehydration}^{polar}$ is positive if the polar function had interacted reasonable well with the water network. Isolated H-bond functions are easily accessible to the water network and thus the H-bonds between these polar functions and the water network can be realized with ideal geometry. However, this seems not to be the case for more complex combinations of H-bond functions such as esters or complex molecules such as proteins for which $\epsilon^{polar \ldots wat}$ can assume any value between $\epsilon_0^{polar \ldots wat}$ and 0 kJ/mol.

As reflected in the quite weak orientation capability, the '—CH•••O H-bond' is with $\epsilon_0 \mp 1$-3 kJ/mol (Gu et al., J. Am. Chem. Soc. 1999, 121: 9411-9422) very weak compared to the H-bond between individual water molecules. Thus, the water H-bond function interacting with the '—CH'-function can be considered to be unsatisfied. In the following, we will refer to a function as apolar if it forms so weak H-bonds to water molecules that it gives rise to an additional unsatisfied H-bond function in the water network. As a consequence, the water molecules surrounding apolar functions have three satisfied and one unsatisfied H-bond function and thus the same fraction of unsatisfied H-bond functions as found in bulk water at 373K or at surfaces i.e. $f_{sat}=0.75$ and $f_{unsat}=0.25$. Thus, the presence of an apolar function gives rise to an increased fraction of unsatisfied H-bond functions in the water network by $(0.25-f_{unsat}(T))$ compared to pure water at temperature T and thus to a lower enthalpy and a higher entropy of the water network. However, the loss of enthalpy is only exactly compensated by a gain in the entropy term of water at the correct temperature. The temperature will be in any case lower than 373K at which the enthalpy/entropy term compensation for $f_{unsat}=0.25$ would occur and therefore the change in the entropy term is not large enough to compensate for the enthalpy loss. Due to the lower temperature than that at which the enthalpy/entropy term compensation would occur, a net unfavorable Gibbs free energy is generated. As a consequence, apolar moieties aggregate in order to minimize the number of additional unsatisfied H-bond functions within the water network and thereby the unfavorable contribution to the Gibbs free energy of the water network.

The change in Gibbs free energy of the water network due to an additional unsatisfied water H-bond function at an apolar function can be calculated by combining $\Delta H$ and $-T\Delta S$ for transferring water from the state characterized by $f_{unsat}$ at temperature T to the state characterized by $f_{unsat}=0.25$ at temperature T:

$$\Delta H = H(T = 373 \text{ K}) - H(T)$$
$$= 0.75 \cdot 4\varepsilon_0^{wat \ldots wat} - f_{sat}(T) \cdot 2\varepsilon_0^{wat \ldots wat}$$
$$= +(0.75 - f_{sat}(T)) \cdot 2\varepsilon_0^{wat \ldots wat} > 0$$

$$-T\Delta S = -T(S(T = 373 \text{ K}) - S(T))$$
$$= T(0.25/373 \text{ K} \cdot 4\varepsilon_0^{wat \ldots wat} - f_{unsat}(T)/T \cdot 2\varepsilon_0^{wat \ldots wat})$$
$$= (0.25 \cdot T/373 \text{ K} - f_{unsat}(T))2\varepsilon_0^{wat \ldots wat} < 0$$

Combining the endothermic enthalpy change with the favorable change in entropy results in:

$$\Delta G_{hydration}^{apolar} = \Delta H - T\Delta S = -\tfrac{1}{2} \cdot \varepsilon_0^{wat \ldots wat}(1 - T/373K) > 0$$

Comparing the enthalpy and entropy term changes for heating bulk water from temperature T characterized by $f_{unsat}(T)$ to the temperature T=373K characterized by $f_{unsat}=0.25$ with those for generating an additional unsatisfied H-bond function at an apolar function, shows that the enthalpy change is identical. However, the entropy term for generating an additional unsatisfied water H-bond function has an additional factor T/373K by which the entropy term is reduced. FIG. 3B shows $\Delta H$, $-T\Delta S$ and $\Delta G$ within the water network for the generation of an additional unsatisfied water H-bond function as a function of the temperature. $\Delta H$ is endothermic at any temperature, and only partly compensated by a favorable $-T\Delta S$ term. On the other hand, the removal of an unsatisfied H-bond function within the water network i.e. the dehydration of an apolar function results in a favorable $\Delta G$ of the same size.

$$\Delta G_{dehydration}^{apolar} = +\tfrac{1}{2} \cdot \varepsilon_0^{wat \ldots wat}(1 - T/373K) < 0$$

The size of $\Delta G_{dehydration}^{apolar}$ is temperature dependent and has its maximum contribution with -3.8 kJ/mol at 273K. It is still -2.9 kJ/mol at 293K, -2.1 kJ/mol at 313K and approaches 0 kJ/mol at T=373K since the enthalpy/entropy term compensation is again valid at 373K.

According to present invention, the hydrophobic effect correlates with the difference of unsatisfied water H-bond functions in the presence and absence of apolar functions and thus will be lower if the fraction of unsatisfied water H-bonds in an aqueous solution is higher than in pure water due to additives. The presence of organic additives leads to a larger fraction of unsatisfied water H-bond functions, $f_{unsat}$, at temperature T compared to that present in pure water at temperature T. $\Delta H$ and $T\Delta S$ for the generation of an additional unsatisfied water H-bond function by an apolar function can be calculated if T' is the temperature at which the fraction of unsatisfied water H-bond functions is $f_{unsat}$, in pure water:

$$\Delta H = H(T = 373 \text{ K}) - H(T')$$
$$= +(0.75 - f_{sat'}) \cdot 2\varepsilon_0^{wat \ldots wat} > 0$$

-continued $$-T\Delta S = -T(S(T=373\text{ K}) - S(T'))$$
$$= -T(-0.25/373\text{ K} \cdot 2\epsilon_0^{wat\ldots wat} + 1/T' f_{unsat'} \cdot 2\epsilon_0^{wat\ldots wat})$$
$$= (T/373\text{ K} \cdot 0.25 - T/T' f_{unsat'})2\epsilon_0^{wat\ldots wat} < 0$$

$$\Delta G_{hydration}^{apolar} = \Delta H - T\Delta S$$
$$= (0.75 - f_{sat'} + T/373\text{ K} \cdot 0.25 - T/T' f_{unsat'})$$
$$2\epsilon_0^{wat\ldots wat} > 0$$

Comparing the enthalpy and entropy terms in the presence and absence of organic additives, it becomes obvious that both the enthalpy and the entropy term change of the water network induced by an apolar function is smaller in the presence of organic additives. In addition, the unfavorable Gibbs free energy, $\Delta G_{hydration}^{apolar}$ becomes less unfavorable due to the presence of the increased fraction of unsatisfied water H-bond functions, however not as much as it would have been if the temperature in the water would be T'. Thus the hydrophobic effect is reduced in the presence of organic molecules.

Figure 3:
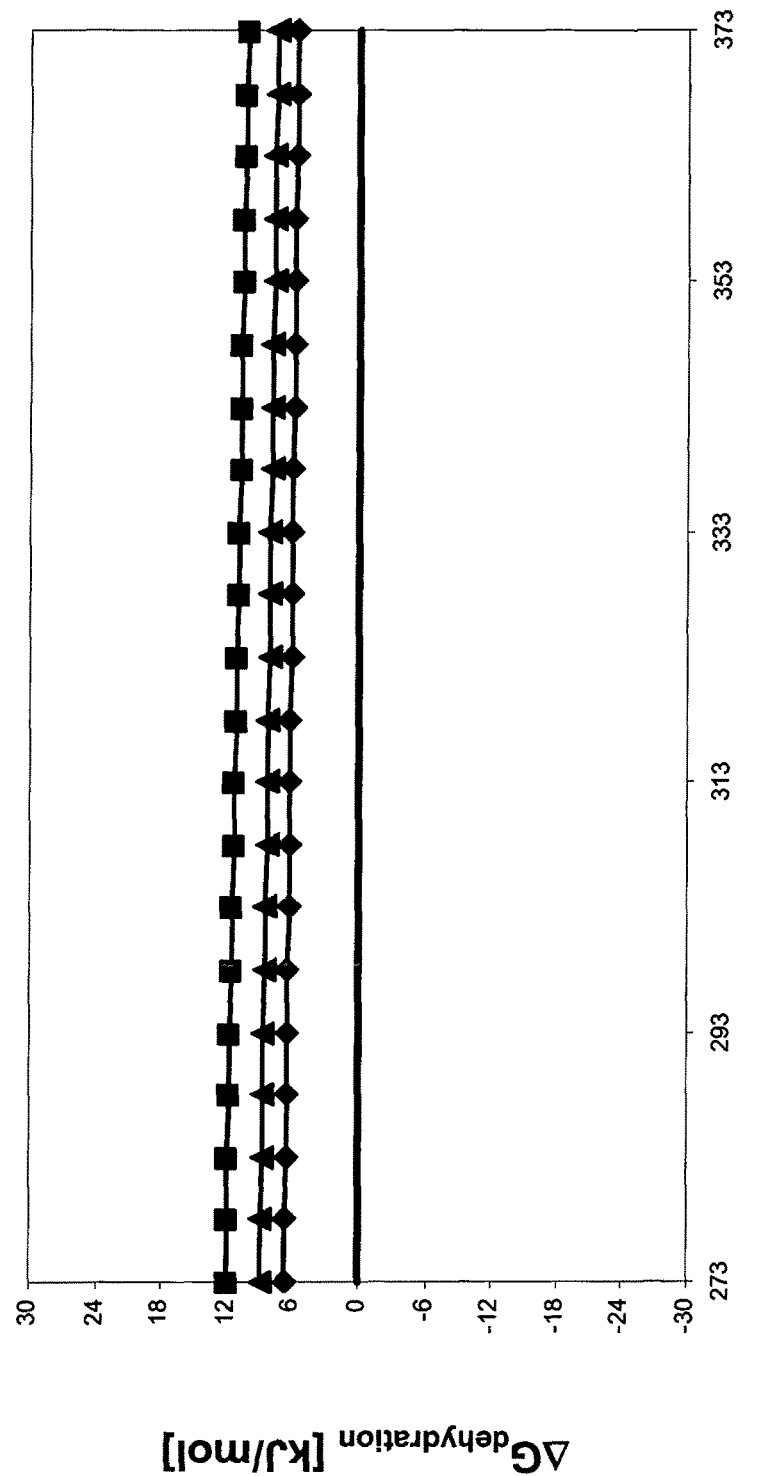
FIG. 3 A shows $\Delta G_{dehydration}$ for an isolated polar function with $\epsilon^{pol\cdots wat}$=27.1 (squares), 20 (triangles) and 15 kJ/mol (diamonds) as a function of the temperature.
Figure 3:
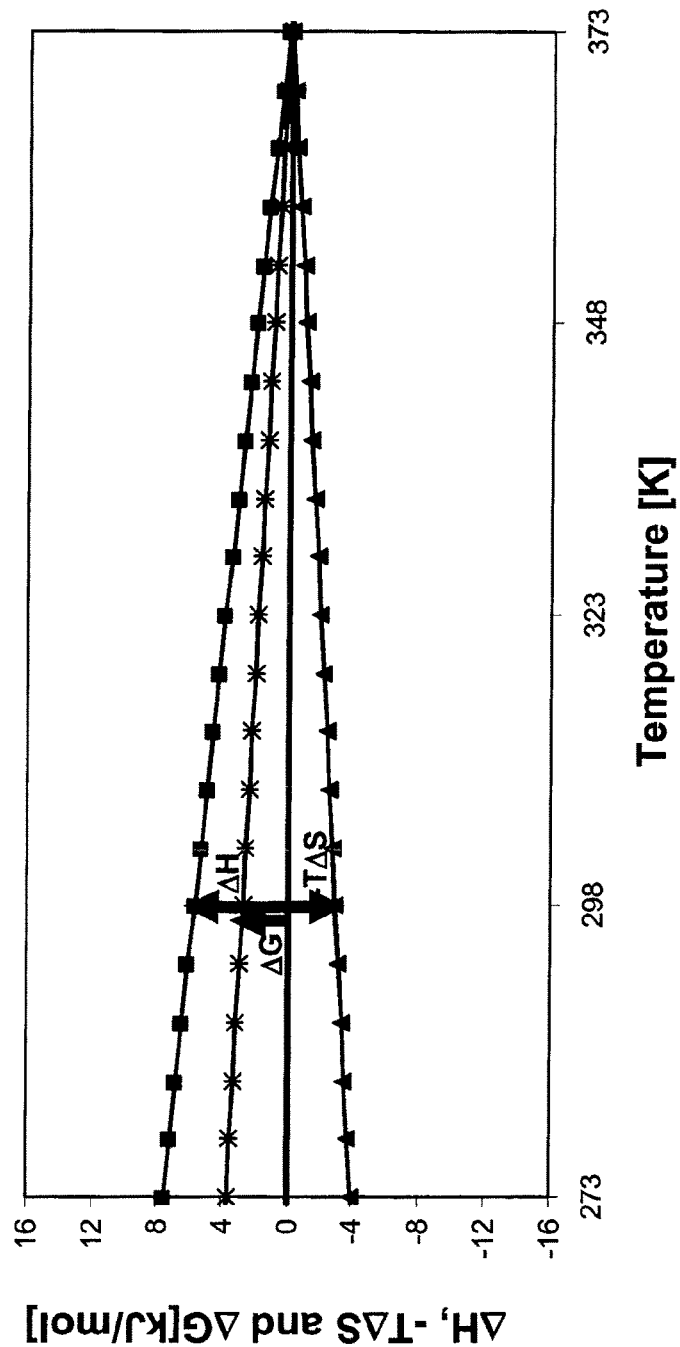
Figure 3:
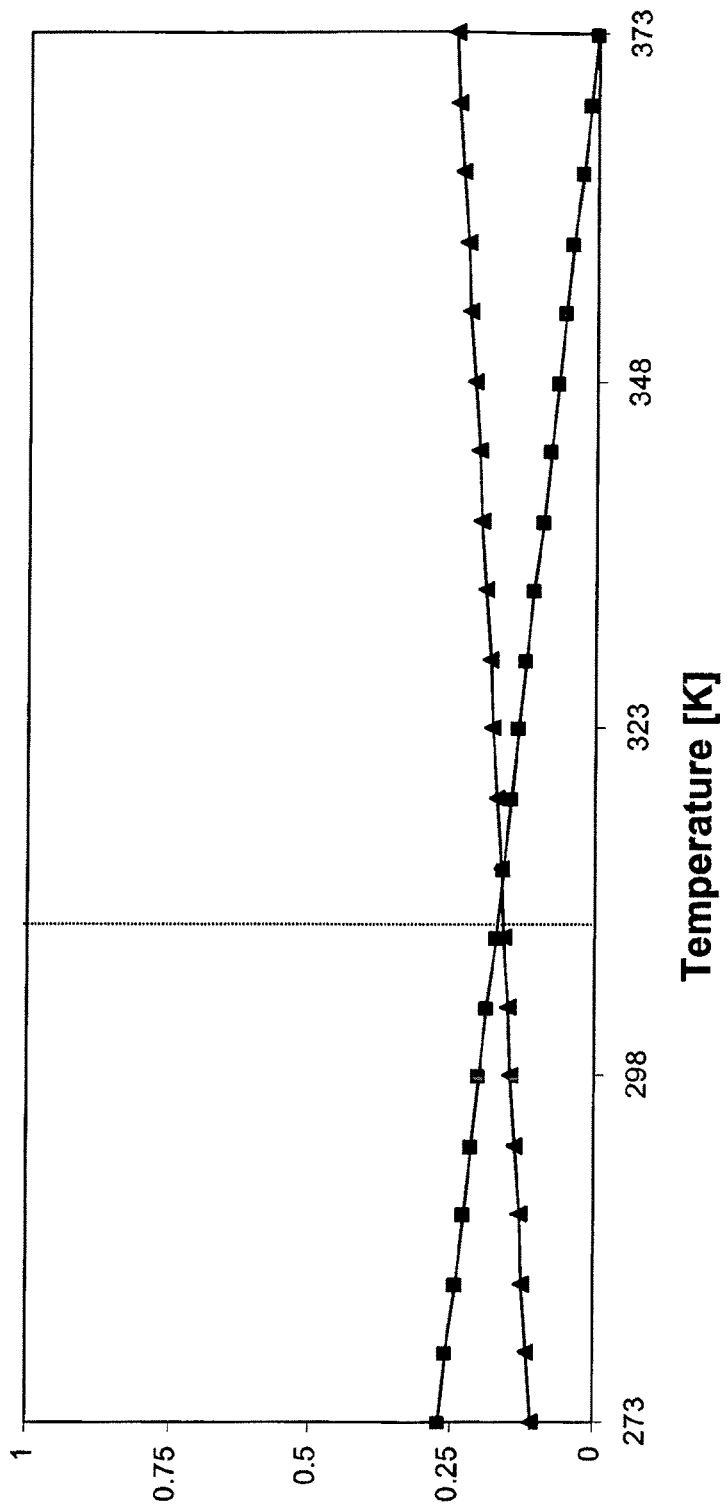

Both, the dehydration of polar and apolar functions are temperature dependent. However, there are two opposite running factors modulating the interaction between a solute and the water network which result directly from the relationship between the enthalpy and entropy term contribution of the H-bonds within bulk water. At low temperatures the (1−T/373K) factor which is caused by the uncompensated enthalpy/entropy terms of the water network in the presence of an apolar function has a larger impact while at higher temperature the correction term $(1-f_{sat}(T))$ which reflects the reduced Gibbs free energy for breaking an H-bond within the water network has a larger impact. The two modulating factors intersect each other at 311.5K (FIG. 3 C).

EXAMPLES

The water specific Gibbs free desolvation energy has an unexpected impact on the interaction between molecules in aqueous solution. Functional groups from different molecules come close to each other in an intermolecular interface. Different pairings of isolated functional groups can occur: (1) two isolated polar functions forming an intermolecular H-bond, (2) two isolated apolar functions forming an apolar contact pair, (3) an isolated polar and an apolar function e.g. a CH . . . O contact pair and (d) those pairings involving functions for which $\epsilon_0^{wat\ldots wat} < \epsilon_0^{func\ldots wat} < 0$ such as —C—F functions. These pairs contribute differently to $\Delta G_{bound/unbound}$. Some contribute favorably ($\Delta G^{i,j} < 0$), while others may contribute unfavorably ($\Delta G^{i,j} > 0$) and are only observed because they are topological forced upon the system if the favorable contributions exceeds the sum of the unfavorable contributions to $\Delta G_{bound/unbound}$. Some examples are listed of how the dehydration determines the contribution $\Delta G^{i,j}$ to $\Delta G_{bound/unbound}$ and how hitherto incomprehensible observations can be readily understood if the dehydration terms derived from present invention are applied.

Example 1

Calculation of the Contribution of Interfacial H-Bonds in Aqueous Solution $\Delta G_{i,j}$ for the formation of an interfacial H-bond can be calculated by combining the Gibbs free dehydration energy of the polar functions ($\Delta G_{dehydration}^{polar}$) with the vacuum H-bond energy of the interfacial H-bond ($\epsilon^{polar1\ldots polar2}$).

$$\Delta G^{i,j} = \epsilon_0^{polar1\ldots polar2} + \Delta G_{dehydration}^{polar} =$$
$$\epsilon_0^{polar1\ldots polar2} - f_{sat}\epsilon_0^{polar1\ldots wat} -$$
$$f_{sat}\epsilon_0^{polar2\ldots wat} + f_{sat}\epsilon_0^{wat\ldots wat}$$

The contribution of an individual interfacial H-bond $\Delta G^{i,j}$ to $\Delta G_{bound/unbound}$ thus depends strongly on the difference in quality between the interfacial H-bond and the H-bonds that the polar functions can form with the water network. In general, if the H-bonds are of similar quality, $\Delta G^{i,j}$ is weakly stabilizing. If the new interfacial H-bond is worse than the H-bonds between the polar functions and the water network, $\Delta G^{i,j}$ is a destabilizing contribution to $\Delta G_{bound/unbound}$. If the new interfacial H-bond is much better, $\Delta G^{i,j}$ becomes a strongly stabilizing contribution to $\Delta G_{bound/unbound}$. However, unless there is a conformational change, the interfacial H-bonds are either of similar quality or worse since water molecules are much smaller and more flexible than most putative interaction partners. In addition, $\Delta G^{i,j}$ depends significantly on the fraction of unsatisfied H-bond functions in the water network.

Many small molecule ligands make H-bonds to the water network with ideal geometry and it can be assumed that $\epsilon^{polar1\ldots wat} \approx \epsilon^{polar2\ldots wat} \approx \epsilon_0^{wat\ldots wat}$. If this is true for both H-bond functions which form an interfacial H-bond, the contribution of this H-bond is the following:

$$\Delta G^{i,j} = \epsilon_0^{polar1\ldots polar2} - f_{sat}\epsilon_0^{wat\ldots wat}$$

Figure 4:
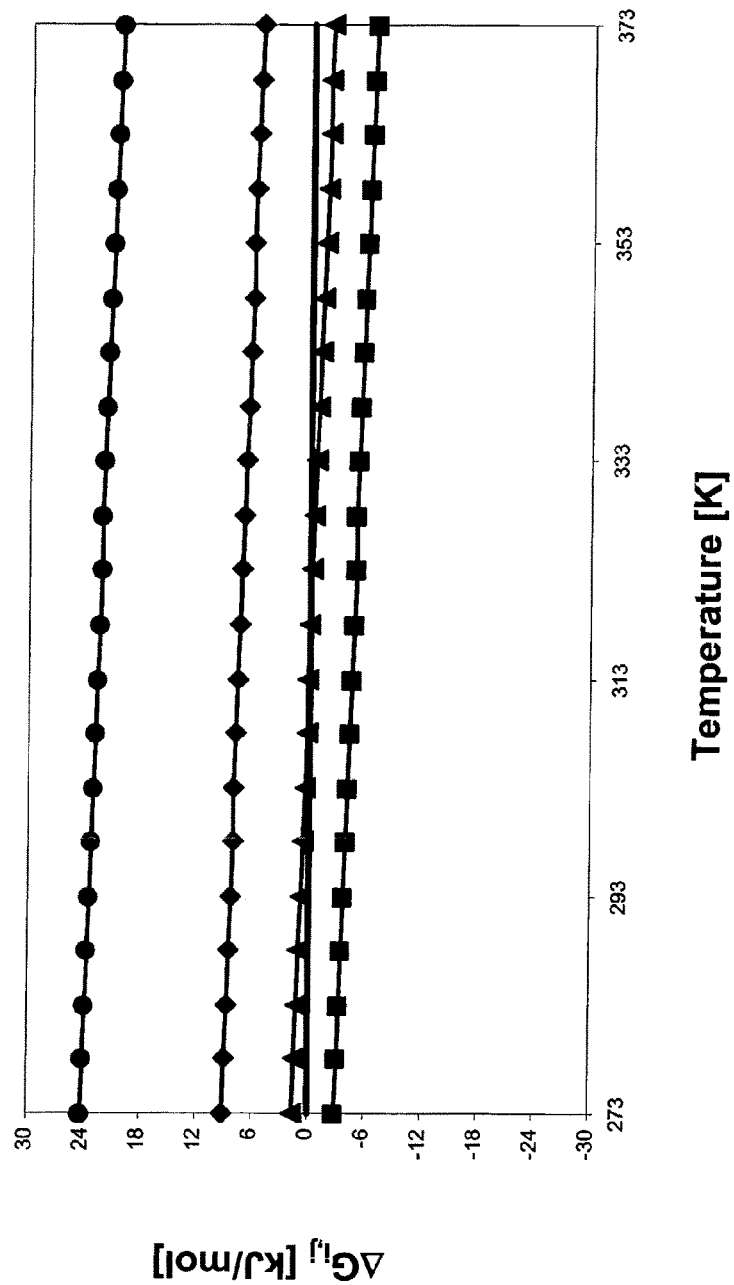
FIG. 4 shows $\Delta G^{i,j}$ if two ideal protein water H-bonds are replaced with an interfacial H-bond of different quality as a function of temperature assuming that $\epsilon^{polar1\cdots polar2}$ is 27.1 kJ/mol (squares), 22.5 kJ/mol (triangles), 15 kJ/mol (diamonds), or 0 kJ/mol (stars).

FIG. 4A shows the change in Gibbs free energy if two ideal H-bond functions which had interacted with water with ideal geometry form an interfacial H-bond with different quality. If the interfacial H-bond has ideal geometry i.e. $\epsilon_0^{polar1\ldots polar2} = -27.1$ kJ/mol, there is a weakly stabilizing contribution $\Delta G^{i,j}$ to $\Delta G_{bound/unbound}$. If the geometry of the new interfacial H-bond deviates so much from the ideal value that $\epsilon^{polar1\ldots polar2} = 0$ kJ/mol, this H-bond represents a strongly destabilizing contribution $\Delta G_{i,j}$ to $\Delta G_{bound/unbound}$. A similar situation to interfacial H-bonds with bad geometry is encountered if either two H-bond donors or two acceptors are facing each other. Also in this case, a similar strong destabilizing contribution to $\Delta G_{bound/unbound}$ of up to 20 kJ/mol at 298K occurs. In addition, the size of the contribution of an interfacial H-bond depends strongly on the fraction of unsatisfied H-bond functions in the water network.

Evidence 1a: Comparison of the Calculation with Experimental Data

Our estimates for the contributions of intermolecular H-bonds to $\Delta G_{bound/unbound}$ are in good agreement with observed experimental values. Various authors estimated that neutral H-bonds generally contribute 2.1-6.3 kJ/mol to $\Delta G_{bound/unbound}$ (Fersht et al., Nature 1985, 314: 235-8, Connelly et al., Proc. Natl. Acad. Sci. U.S.A. 1994, 91: 1964-8). The contributions of amino acid side chains to the binding of tyrosine in the transition state were calculated based on measurements of kcat/Km of mutated tyrosyl-tRNA synthetase. Mutation of a side chain which formed an uncharged H-bond with the substrate decreased the binding energy by only 2.1-6.3 kJ/mol. It should be pointed out, that this holds true only for H-bonds which do not change their geometry such as that to Gln195. Mutating a protein side chain which forms an unusually 'long H-bond' actually improved binding confirming that a poor H-bond destabilizes the binding of the substrate to the protein ($\Delta G^{i,j} > 0$) (Fersht at al., Nature 1985, 314: 235-8).

Evidence 1b: Explanation of the Role of Water in Biological Processes

There is a widely believed prejudice that replacing a water molecule in a protein ligand interface should improve ligand affinity. However, in some cases this was difficult to achieve.

For instance, replacement of the conserved water molecule in the HIV-protease complex was only achieved using cyclic ureas as ligands. Two well defined and highly conserved water molecules are located in the interface between the SH2 domains and their cognate peptides. Several attempts to replace the water molecules while maintaining ligand affinity were unsuccessful. This shows that, currently, no general rules are available in order to predict by how much the replacement of a particular water molecule stabilizes or even destabilizes the protein ligand interface.

Water represents one of the smallest possible interaction partners to the protein and if larger molecules such as substrates are able to form ideal H-bonds to the protein, the replaced water molecule can also bind with ideal H-bond geometry. FIG. 4A shows that an interfacial H-bond contributes weakly stabilizing to $\Delta G_{bound/unbound}$ only if it has an ideal geometry. In all other cases an interfacial H-bond contribute either not at all or in most cases destabilizing. A closer analysis of the H-bonds which the conserved water molecule forms to the HIV-protease shows that the distances and the angles are ideal. As seen above only ligands forming similarly good H-bonds to the protein can replace an ideal bound water molecule without a net loss of stabilization and indeed the reported cyclic urea derivates form H-bonds with similar good geometry to the HIV protease as the conserved water molecule. Recently, we reported crystal structure of closely related non-peptidic inhibitors bound to the SH2 domain of src (Lange et al., J. Med. Chem. 2002, 45: 2915-22). These inhibitors were found in three different binding modes involving one, two or no water molecules. The most common binding mode, which is closely related to that of the cognate peptide, has the water molecules bound in a perfect H-bond network. In addition, all other interfacial H-bonds between the peptides and SH2 have ideal geometry. The binding mode with no interfacial water molecule was found only once. Surprisingly, this inhibitor had a much reduced affinity (2700 nM compared to 4 nM) even though the corresponding inhibitor moieties should give rise to a similar contributing hydrophobic effect. A closer look at the H-bonding showed that all but one interfacial protein ligand interactions have good H-bond geometry. The destabilization due to this far from ideal H-bond explains the surprisingly low affinity. It should be pointed out that individual water molecule once they are enclosed in protein ligand interface have to be treated as ordinary ligands since they are not part of the water network anymore.

Evidence 1c: Explanation for the Phenomenon of Temperature Driven Self Assembly

The driving force of protein self-assembly processes is still poorly understood. Many authors attribute these processes to the hydrophobic effect (Vulevic et al., Biophysical Journal 1997, 72: 1357-75). However, recently, doubts have been expressed and it has been suggested that instead the formation of H-bonding may play an important role in self-assembly processes (Leikin et al., Structural Biology 1995, 2: 205-210). Leikin et al. showed by directly measuring the intermolecular forces during the temperature induced collagen assembly that the free energy estimated from the integrated observed attractive forces increased approximately linearly with the temperature. Another example for self-assembly represents the aggregation of tubulin. Tubulin forms well defined hollow cylinders, the microtubuli, upon temperature increase. Calorimetric measurements have shown that these temperature driven self-assembly processes are entropy driven. Since it seems difficult to comprehend that the formation of well ordered supramolecular structures from individual protein molecules results in an increase of entropy, it was assumed that the increase in entropy was due to not understood processes within the water (Oosawa and Asakura, Thermodynamics of the Polymerization of Protein 1976, Publisher: Academic, London).

According to present invention, the contribution of interfacial H-bonds becomes more favorable with increasing $f_{unsat}$ in the water network due to the reduced Gibbs free dehydration energy of polar functions. In particular, interfacial H-bonds with ideal geometry become more stabilizing. These H-bonds orient two molecules well due to their restrictive H-bond geometry thereby giving rise to well-ordered structures. As a consequence of these stronger stabilizing contributions at higher temperature, the equilibrium is shifted towards the aggregated state with a substantial number of interfacial H-bonds and well ordered supramolecular structures are formed. The importance of interfacial H-bonds in the aggregation of tubulin is reflected in the 3D structure of tubulin. Most of the surface is covered by polar amino acids which form an intricate H-bond network between individual tubulin molecules. Present invention shows that there is a direct connection between the stronger favorable contributions of interfacial H-bonds at higher temperatures and an entropy increase within the water network due to the higher fraction of unsatisfied water H-bond functions at higher temperatures. According present invention, there should be a similar effect if $f_{unsat}$ is enlarged by other means such as by adding organic additives. Time resolved small angle scattering experiments confirm that entropy driven self-assembly processes can be indeed induced by adding dimethylsulfoxid or glycerol confirming that the unsatisfied water H-bond functions within the water network are the underlying cause for temperature induced self-assembly processes. High temperature and the presence of dimethylsulfoxid or glycerol favor microtubuli formation while low temperature shifts the equilibrium towards the disassembled state (Lange et al., Eur. J. Biochem. 1988, 78: 61-69).

Example 2

Calculation of the Contribution of an Apolar Contact Pair in the Intermolecular Interface If an apolar function is transferred into the water network, a positive Gibbs free energy of hydration, $\Delta G_{hydration} = -\frac{1}{2}\epsilon_0^{wat\cdots wat}(1-T/373K)$ kJ/mol, has to be paid due to the disturbance of the water network. This unfavorable contribution to the Gibbs free energy of the water network is released upon removal of the apolar function from the water network. Since two apolar functions are buried against each other in an intermolecular apolar contact pair, the gain in Gibbs free energy for the formation of an apolar contact pair has to be counted twice:

$$\Delta G^{i,j} = -2\Delta G_{dehydration}^{apolar} = \epsilon_0^{wat\cdots wat}(1-T/373) < 0$$

The size of the apolar surface which gives rise to an unsatisfied water H-bond function can be estimated based on geometrical considerations. It corresponds to the surface of the cone of a water H-bond function and can be calculated assuming a distance of 1.6 Å (H-bond distance between oxygen and next water hydrogen) and an angle of 60° for the —O—H•••O angle. This surface is roughly 24 Å$^2$ and very similar to the size of a —C—H group. Thus, the removal of an additional unsatisfied water H-bond function due to the removal of a surface from the size of a —C—H group from the water network releases 2.9 kJ/mol or 113 J/molÅ$^2$ at 298K, 2.1 kJ/mol or 88 J/molÅ$^2$ at 313K and 1.3 kJ/mol or 54 J/molÅ$^2$ at 333K. At 373K, the enthalpy entropy term compensation is again valid and $\Delta G^{i,j}=0$. Correspondingly, the contribution of an apolar contact pair in the intermolecular interface is 5.9 kJ/mol at 298K, 4.2 kJ/mol at 313K and 2.5 kJ/mol at 333K. If the apolar function has a larger surface than a —CH moiety, it will leave more water H-bond functions unsatisfied and induce a larger hydrophobic effect.

Evidence 2: Comparison of the Calculation with Experimental Data

An experimental value for the Gibbs free energy for removing apolar functions from water was obtained from a least-squares fitting of five atom types to the experimental free transfer energy from octanol to water (Eisenberg and MacLachlan, Nature 1986, 319: 199-203). Eisenberg and MacLachlan estimated that the removal of a carbon atom from water corresponds to a 'hydrophobic free energy' of 67 J/mol Å$^2$ without specifying the temperature. Other authors reported that the removal of a hydrophobic surface of the size of a methyl group gives rises to a Gibbs free energy of roughly 117 kJ/molÅ$^2$ at 298K corresponding to approximately 2.9 kJ/mol per methyl moiety (Hermann J. Phys. Chem. 1972, 76: 2754-9; Searle et al., J. Am. Chem. Soc. 1992, 114: 10697-10704). Thus, our calculated values are in excellent agreement with the experimental data. Present invention also describes correctly, that hydrophobic compounds have a higher solubility in the presence of organic additives. As observed in daily life and predicted by present invention correctly, the hydrophobic effect decreases and thus the solubility of hydrophobic compounds increases at higher temperatures and/or in the presence of organic solutes due the predicted better enthalpy/entropy term compensation at higher temperatures. The octanol-water partition coefficients (log $K_{octanol/water}$) of several chlorobenzenes were measured over the temperature range 278 to 318K and found to decrease linearly with the temperature indicating that at higher temperatures the transfer free energy of apolar compounds from octanol to water becomes less unfavorable (Bahadur et al., J. Chem. Eng. Data 1997, 42: 685-688).

Example 3

Calculation of the Contribution of —CH . . . O Contact Pairs in Aqueous Solution If an apolar function faces an H-bond function in the intermolecular interface, one needs to take into account that even though it is of advantage to remove the unfavorable contribution to the Gibbs free energy of the water network in the presence of an apolar function, it is counterbalanced by the Gibbs free energy which is needed to dehydrate the polar function. Thus, the contribution $\Delta G^{i,j}$ to $\Delta G_{bound/unbound}$ is:

$$\Delta G^{i,j} = -\tfrac{1}{2} \cdot \epsilon_0^{wat \ldots wat}(1 - T/373) - f_{sat}\epsilon^{polar \ldots wat} + \tfrac{1}{2} f_{sat}\epsilon_0^{wat \ldots wat}$$

Figure 5:
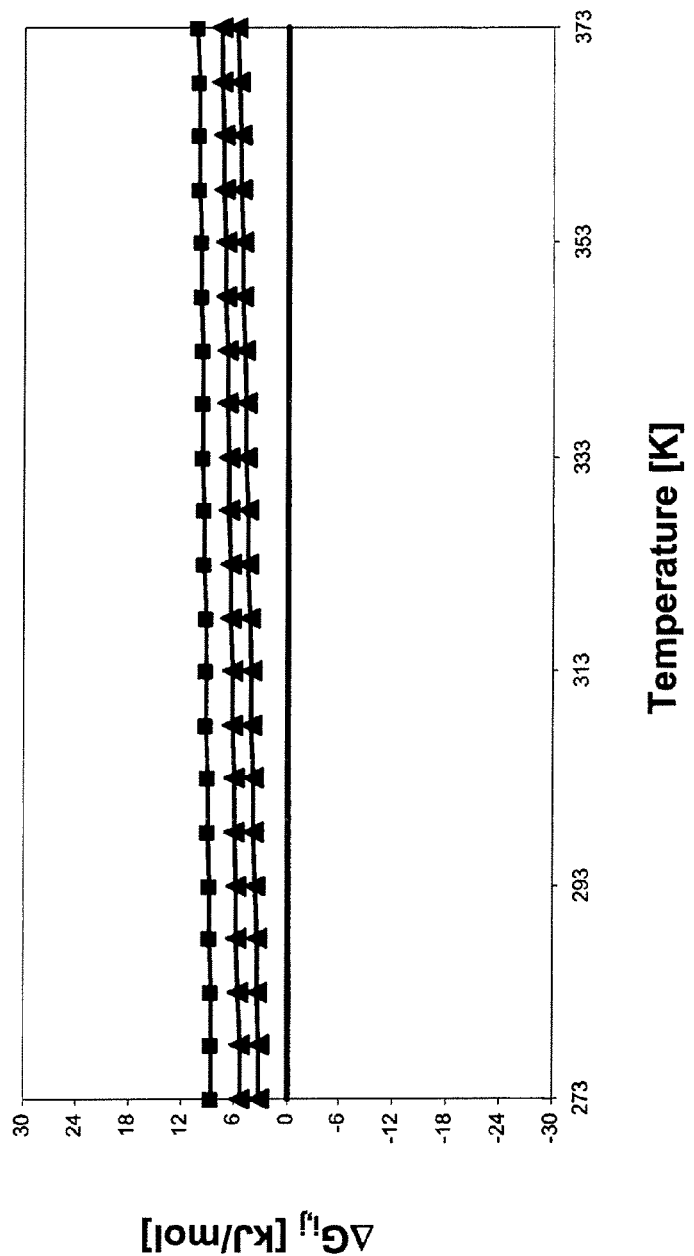
FIG. 5 shows $\Delta G^{i,j}$ for generating a CH . . . OR contact pair in an interface as a function of temperature assuming that the water was bound to the H-bond function with either 27.1 (squares), 20 (triangles) or 15 (diamonds) kJ/mol.

The contribution $\Delta G^{i,j}$ to $\Delta G_{bound/unbound}$ depends on the fraction of unsatisfied H-bond function within the water network and the quality of the H-bond between the polar function and the water network. For instance at 298K, the benefit due to the dehydration of the apolar function of −2.7 kJ/mol is counterbalanced by +11.5 kJ/mol which are required to dehydrate the polar function if the water had been H-bonded with ideal geometry. This results in a net destabilization with $\Delta G_{bound/unbound}$ equals +8.8 kJ/mol. FIG. 5A shows $\Delta G^{i,j}$ as function of temperature for creating a —CH . . . OR contact pair assuming that the polar function had been integrated into the water network with different geometry. While the removal of an apolar surface from the water network becomes less favorable with increasing $f_{unsat}$, the penalty for dehydrating a polar decreases only slightly. As a result, the formation of a —CH . . . OR contact pair becomes more unfavorable with increasing temperature.

Evidence 3a: Explanation for the Specificity in Intermolecular Interfaces

Molecular recognition and ligand specificity has been generally assumed to be conferred by made H-bonds between the interacting molecules. Recently, doubts have been expressed if the selectivity in protein ligand complexes indeed originates from the H-bonds in the protein ligand interface since the experimentally obtained contribution of an interfacial H-bond is with 2.1-5.0 kJ/mol so small that it cannot explain the observed selectivity (Kool 2001). Instead it has been proposed that a preferred binding might origin in the favorable contribution of the 'hydrophobic interactions' (Kool, Annu. Rev. Biomol., Struct. 2001, 30:1-22). Other authors (Klaholz and Moras, Structure 2002, 10: 1197-1204; Pierce et al., Proteins: Structure, Function, and Genetics 2002, 49: 567-576) have suggested that intermolecular 'C—H • • • OR interactions' introduce both specificity and affinity within the intermolecular interface. The nature and importance of the 'CH • • • OR interactions' is currently very much under discussion. The small size of $\epsilon_0^{CH \ldots OR}$ seems to indicate to some that their stabilizing contribution is insignificant and can be ignored in ligand design. Other authors proposed that they have a significant stabilizing contribution which should be exploited in drug design (Klaholz et al., Structure 2002, 10: 1197-1204; Pierce et al., Proteins: Structure, Function, and Genetics 2002, 49: 567-576). Thus, the origin of selectivity and in particular the role of '—CH . . . OR H-bonds' remains unclear but can be seen in a new light if the dehydration terms for polar and apolar functions derived above are applied. In addition, applying present invention it becomes clear how nature achieves to combine low affinity with high specificity, a binding characteristic which has been widely observed but was hitherto not understood.

Specificity/recognition means that the system has to be able to distinguish between correct and wrong ligands. This can be achieved by favoring those compounds which make stabilizing interactions but also by disfavoring ligands with destabilizing interactions. As seen in x-ray structures, selectivity seems to be conferred by ideal interfacial H-bonds which were formed after an ideally bound water has been replaced. According to present invention, the contribution of a protein ligand H-bond towards stabilization of a protein ligand complex is at best app −4.0 kJ/mol at 298K which gives rise to a modest 5-10 fold increased affinity. On the other hand, each unsatisfied interfacial H-bond function disfavors complex formation by up to +11.5 kJ/mol at 298K giving rise to a net destabilization of 8.8 kJ/mol for '—CH . . . O H-bonds' and 20 kJ/mol for interfacial 'H-bonds' with bad H-bond geometry. In the first case this leads to a 10-50 fold destabilization while the destabilization in the latter case is 5000 fold. Thus, for instance, $\Delta\Delta G$ between binding a ligand which forms the 'correct H-bond with ideal geometry' and a ligand which makes a 'not correct CH . . . O contact pair' is roughly 9.0 kJ/mol corresponding to a 100 fold lower binding for the wrong ligand. If there are instead of the two correct H-bond partners, two H-bond donors or acceptors present in the interface, $\Delta\Delta G=20$ kJ/mol corresponding to 10000-100000 fold lower affinity. This shows that nature achieves to combine low affinity binding with high specificity by favoring ligands with stabilizing H-bonds but even more by disfavoring ligands with destabilizing contributions to $\Delta G_{bound/unbound}$.

Results from a novel approach which uses protein crystallography for the screening of a low affinity fragment library have been analyzed by comparing the X-ray structures with bound fragments to the structures with corresponding full length inhibitors (Lange et al., J. Med. Chem. 2003, 46: 5184-5195). The x-ray data show that the millimolar binding fragments are recognized by forming a complex H-bond network within the phospho-tyrosine pocket of SH2. No fragment x-ray structure was found in which this H-bond network was incomplete and any unsatisfied H-bond function within the H-bond network leads to a significant decrease in the affinity of full length inhibitors. For instance, the loss of a single interfacial H-bond resulted in a decrease of the $IC_{50}$ from 4 nM to 450 nM. The surprisingly large affinity decrease cannot be explained by the lack of the stabilizing protein ligand H-bond only. However, interpreting it as replacement of a favorable protein ligand H-bond ($\Delta G^{i,j} \approx -4.0$ kJ/mol) with an unfavorable contribution due to an unsatisfied interfacial protein H-bond function ($\Delta G^{i,j} \approx +8.8$ kJ/mol) results in a $\Delta\Delta Gi,j=12.8$ kJ/mol for binding the correct or the wrong ligand which explains the 100 fold decrease in affinity.

The importance of a complete H-bond network in nucleotide recognition has been investigated. Molecular recognition usually involves several H-bonds. The influence of unsatisfied interfacial H-bond functions can be seen in the destabilization of a helix in which thymidin is replaced by difluortoluoldesoxynucleosid. The experiments have shown that these helices exist in aqueous solution but are destabilized by 16 kJ/mol compared to the helices with thymidin (Moran et al., J. Am. Chem. Soc. 1997, 119: 2056-2057). The authors conclude that the specificity of base pair recognition may not be due to H-bonding but to space filling since the modified base is incorporated into the double helix even though the H-bond cannot be made. However, it should be pointed out that a destabilization of 16 kJ/mol corresponds to a 1000-10000 times reduced affinity and in the presence of equimolar thymidin the wrong nucleosid difluortoluoldesoxynucleosid would only be inserted in 1 out of $10^4$ cases. This value agrees well with the mismatched pairing observed for the incorporation of nucleotides into DNA by polymerase enzymes (1 in $10^3$-$10^5$) (Loeb and Kunkel, Annu. Rev. Biochem. 1982: 52, 429) and the preference of correct tRNA compared to near cognate tRNA in the codon:anticodon recognition (1 in $10^{-3.5}$) (Thompson and Karim, Proc. Natl. Acad. Sc. U.S.A. 1982, 79: 4922-26).

Example 4

Figure 6:
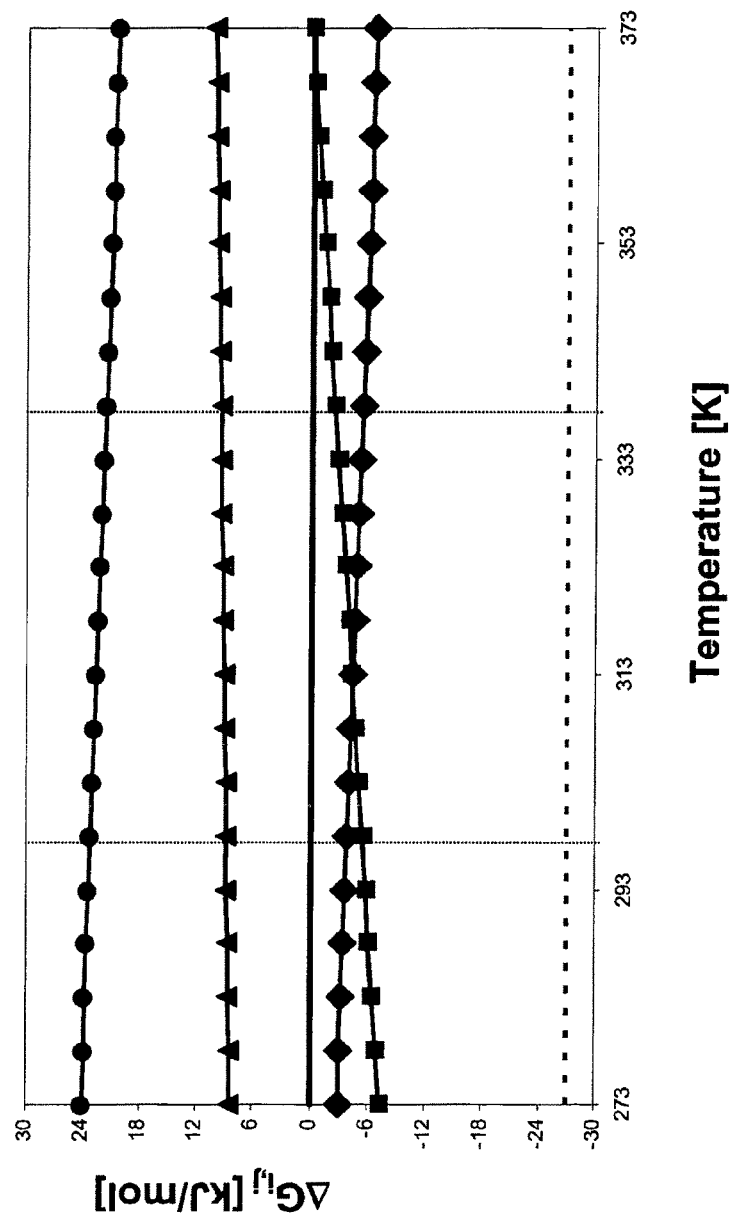
FIG. 6 shows $\Delta G^{i,j}$ for creating an apolar contact pair (squares), a CH . . . OR (triangles) contact pair assuming that $\epsilon^{polar\cdots wat}$=27.1 kJ/mol, an ideal interfacial H-bond (diamonds), the most unfavorable interfacial H-bond (stars) and the most favorable interfacial H-bonds (dashed line) in the intermolecular interface as a function of temperature. The latter can be only formed after a conformational change within the molecules and is shown therefore in a dashed line. The dotted lines mark the temperature T=298K and T=338K in pure water.

Calculation of the Balance Between Individual Interaction Types as Function of the Unsatisfied Water H-Bond Functions in Aqueous Solution The balance between stabilizing and destabilizing contributions $\Delta G^{i,j}$ is strongly dependent on $f_{sat}$ and $f_{unsat}$ and thus the temperature (FIG. 6 A). At room temperature, the stabilization due to the burial of apolar moieties is significantly higher than the stabilization due to interfacial H-bonds. Interfacial H-bonds which are of similar quality to those the polar functions had originally made to the water network are slightly stabilizing. Replacing water H-bonds of polar functions with an interfacial H-bond which is not as good as the original H-bond to water, gives rise to a significant destabilization. A similar high destabilization occurs if two H-bond donors or acceptors face each other in the interface since no H-bond energy compensates for the dehydration of the polar functions. In contrast, the removal of an H-bond between a polar function and the water network with bad geometry, contributes strongly favorably to $\Delta G_{bound/unbound}$ but can only be realized if the protein undergoes a conformational change.

Another destabilization is contributed by an unsatisfied H-bond function in the intermolecular interface if it had been able to interact with good geometry to water. There are two opposite running factors modulating the interaction between a solute and the water network with increasing temperature (FIG. 3 C). Due to the larger $f_{unsat}$ at higher temperatures, the stabilizing contribution of an interfacial ideal H-bond increase roughly by 0.042 kJ/molgrd with the temperature. The destabilization due to not correctly made intermolecular H-bonds becomes smaller. Most importantly, the hydrophobic effect becomes weaker with increasing temperature. Thus, at temperatures above 330K, there are completely different stabilizing and destabilizing contributions which favor different interfaces at higher temperatures.

Evidence 4a: Comparison of the Calculation with Experimental Data

A temperature dependent shift of the balance between different interaction types has been observed in the neutron scattering data of a diluted tertiary butanol solution (Bowron et al., J. Chem. Phys. 2001, 114: 6203-6219). An analysis of the temperature dependence of a solution of a 0.06 mole fraction of tertiary butanol in water showed that major changes are seen only in the interaction between the tertiary butanol molecules. The structure of water in the solution seems not to change significantly with temperature. Based on our estimate, the average H-bonds per water molecule would decrease from 3.4 at 298K to 3.2 at 338K. This may well lie within the experimental error found for neutron scattering experiments of liquids. In contrast, the preferred interaction between individual tertiary butanol molecules changes significantly with temperature. While at 298K the contacts between the apolar moieties seem to dominate the solute-solute pair correlation function, there is an increase in direct H-bonding between the hydroxyl groups of the tertiary butanol molecules at 338K suggesting that the hydrophobic effect looses its importance at higher temperatures. No explanation for this observation was given (Bowron et al., J. Chem. Phys. 2001, 114: 6203-6219). According to present invention, $\Delta G^{i,j}$ for the formation of an ideal interfacial H-bond equals $-3.9$ kJ/mol at 298K compared with $\Delta G^{i,j}=-5.4$ kJ/mol for the formation of an apolar contact pair indicating that the formation of an apolar contact pair is significantly preferred at 298K. At 338K, $\Delta G^{i,j}$ for the formation of an apolar contact pair is $-2.5$ kJ/mol while the contribution of an ideal interfacial H-bond is $-5.4$ kJ/mol. Thus at 338K, the formation of an H-bond between two tertiary butanol molecule has a similar preference than the formation of an apolar contact pair which explains the experimental observation.

Evidence 4b: Explanation for 'Enthalpy/Entropy Compensation in Weak Interactions'

It has been observed in experiments that for 'weak' interactions' such as protein ligand, $\Delta G_{bound/unbound}$ is not strongly dependent on temperature (Calderone and Williams, J. Am. Chem. Soc. 2001, 123: 6262-7). Even though the enthalpy and the entropy taken on their own have often substantial values, it was found experimentally that they compensate each other thus giving rise to a small value for $\Delta G_{bound/unbound}$. It had been suggested that it is intuitively clear that stronger interaction between molecules will result in a reduction of the configurational freedom of the system and thus a reduction of entropy. However, temperature induced self-assembly and specific experiments (Gallicchio et al., J. Am. Chem. Soc. 1998, 120: 4526-4527) show that the enthalpy/entropy compensation is not a general thermodynamic requirement and enthalpy/entropy compensation remains unexplained. Alternatively, the phenomenon of enthalpy/entropy compensation in weak intermolecular interaction might be explained by the different temperature dependence of $\Delta G^{i,j}$ for different atomic interaction types. According to present invention, some interaction types become more favorable while others become more unfavorable with increasing temperature. If there is a fair distribution of H-bonds and apolar contact pairs in the intermolecular interface, the different temperature dependencies annihilate each other giving rise to a seemingly temperature independent $\Delta G_{bound/unbound}$. However, $\Delta G_{bound/unbound}$ becomes temperature dependent if either polar or apolar functions strongly dominate the molecular interface, If the interface is dominated by H-bonds, $\Delta G_{bound/unbound}$ will become more favorable with increasing temperature. This is the case for temperature induced self-assemblies (see example 1). If the interface is dominated by apolar contact pairs, $\Delta G_{bound/unbound}$ will become less favorable with increasing temperature and/or presence of organic additives.

Evidence 4c: Explanation for the Phenomenon of Protein Denaturation

As seen above the balance between individual interactions types depends strongly on the temperature and the fraction of unsatisfied H-bond functions in the water network. Proteins form complicated three-dimensional structures which consist of α-helices and β-sheets. The maximal stability of the protein structures is at room temperature and heat-induced denaturing of proteins occurs roughly between 313 and 333K. The reason for this unfolding has been widely investigated but is still not fully understood.

Figure 7:
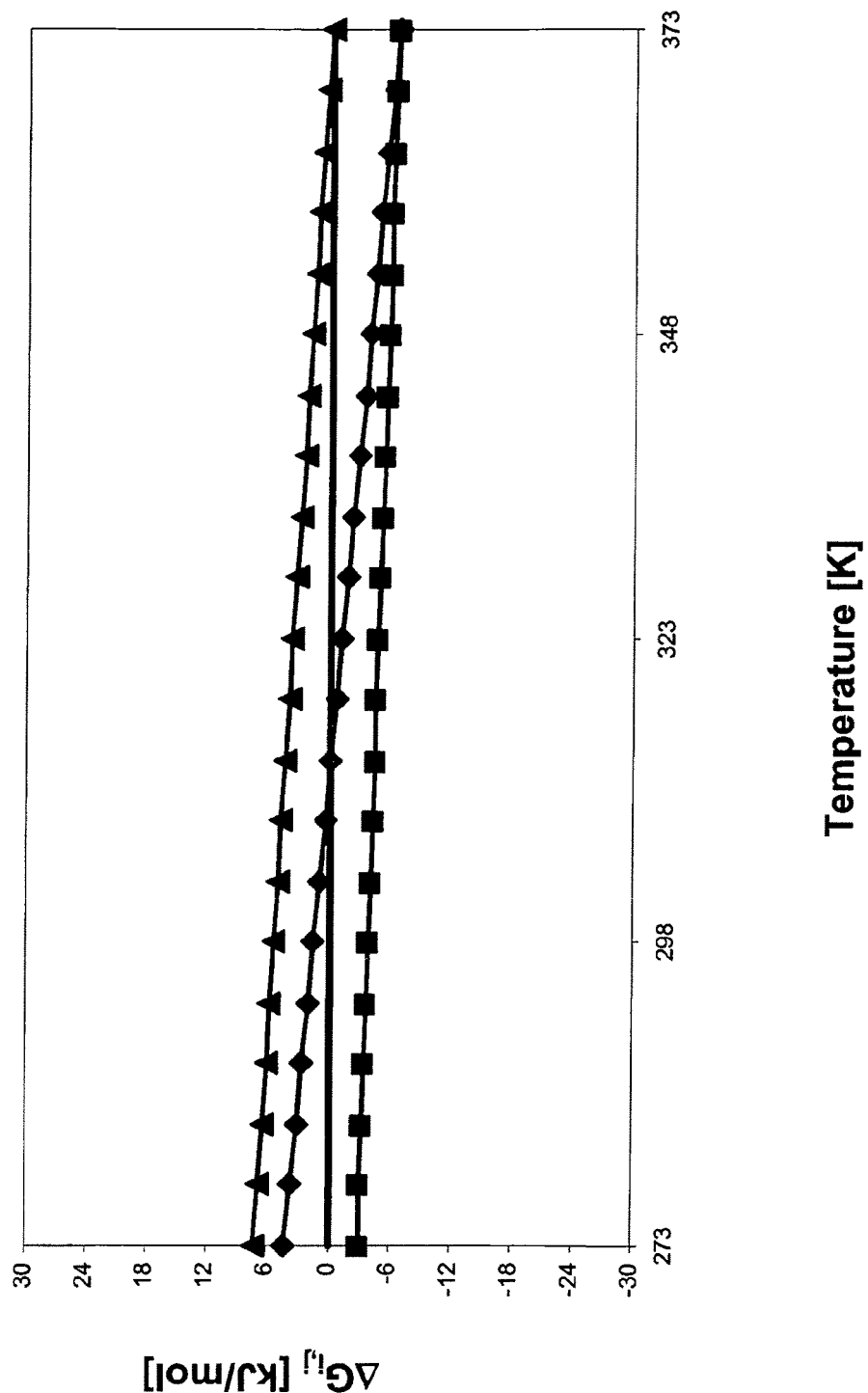
FIG. 7 shows that the folded protein state becomes more unfavorable with higher temperature since $\Delta G^{i,j}$ for the formation of an additional ideal interfacial H-bond (squares) becomes more favorable and the unfavorable $\Delta G^{i,j}$ for the exposure of an apolar moiety to water (triangles) becomes less severe. Their sum (diamonds) shows that both effects annihilate each other at 313K.

According to present invention, there is a simple explanation for the different preferred structural elements of polyamino acid chains at lower temperatures. At temperatures below 313K, the main stabilizing contribution for the 3D protein structure formation comes from the burial of apolar functions against each other while there is a significant destabilization of protein structures due to the presence of unsatisfied interfacial protein H-bond functions within the protein while ideal interfacial H-bonds contribute only weakly (Savage et al., J. Chem. Soc. Faraday Trans. 1993, 89: 2609-17). However, with increasing $f_{unsat}$ and/or temperature the balance is changing. The formation of interfacial H-bonds becomes stronger stabilizing and the burial of apolar functions becomes less of a requirement (FIG. 7 A). At temperature above 313K, the formation of an additional interfacial H-bond is stronger stabilizing than the destabilization due to the exposure of an additional apolar function to the water network and thus the three dimensional structure which was stable at room temperature unfolds. The balancing of the different atomic interaction types is crucial for the formation, the stability and the possibility for folding/unfolding of three-dimensional protein structures. A significant contribution due to ideal interfacial H-bonds is needed since due to their directionality ordered three dimensional structures such as β-sheets and α-helices are formed. On the other hand, the hydrophobic effect is required for thermodynamic stability. Since these two contributions depend from $f_{unsat}$ in the opposite direction, protein structures are only stable in a limited region in which $f_{unsat}$ is still so small that the hydrophobic effect has a significant value but is already large enough to induce secondary structure formation via ideal H-bonds.

Similar to a temperature increase, the fraction of unsatisfied H-bond functions is increased in the presence of organic additives such dimethylsufoxid, glycerol or Trifluoroethanol. Indeed, it has been observed that these additives lead to a stabilization of internal protein H-bonds and to a reduction of the hydrophobic effect. Trifluoroethanol has been reported to stabilize helices and proteins by strengthening the intramolecular H-bonds (Cammers-Goodwin et al., J. Am. Chem. Soc. 1996, 118: 3082-90; Luo et al., J. Mol. Biol. 1998, 279: 49-57). It has also been observed, that in the presence of trifluoroethanol and hexanediol the disordered switch II region of Ras protein is ordered since key H-bonds seem to be enhanced in the presence of these organic solvents (Buhrmann et al., Structure 2003, 11: 747-751).

Example 5

Calculations of the Interaction Between Two Molecules in Aqueous Solutions

Scoring functions are used in order to calculate the interaction between two molecules in a more automatic fashion. Most scoring functions sum up individual terms for intermolecular interactions such as H-bonds, 'hydrophobic interaction', and 'CH . . . O' interactions. The physical meaning of the terms $\Delta G^{i,j}$ described in examples 1-3 compare directly with the terms used in most scoring functions. However, the size and the sign of the contributions calculated according to present invention differ significantly from those used in other scoring function. For instance, the scoring function used in docking programs such as FlexX (Rarey et al., J. Mol. Biol. 1996, 261: 470-489,) rewards the formation of interfacial H-bonds much higher than contributions due to the hydrophobic effect. As a consequence, the effects due to the formation of interfacial H-bonds are overestimated and those docking solutions which have a maximum of interfacial H-bonds are scored most highly. Since the hydrophobic effect is not the result of a force, it is impossible to describe the hydrophobic effect using force fields and thus force-field based approaches have a principle problem. Nevertheless, Kellog et al. (2001) derived a force field based on log $P_{octanol/water}$ in order to empirically include the dehydration into his scoring function (Kellog et al., J. Comp.-Aided Mol. Des. 2001, 15: 381-393). An interaction propensity based on its partial log $P_{o/w}$ was assigned to each atom in a molecule. The interaction score between two atoms in the interface is calculated via an empirical mathematical function treating all interaction types on purpose identical. A logic function derived from 'common understanding' determines if the interaction pair contributes stabilizing (hydrophobic hydrophobic interaction or acid-base interaction) or destabilizing (hydrophobic polar, base-base or acid-acid) contribution to the free binding energy. Additional empirical terms for considering the 'increased entropy in water due to released water molecules' and a calibration for each molecular system has been shown to be necessary in order to explain the experimental results with sufficient accuracy (Cozzini et al., J. Med. Chem. 2002, 45: 2469-2483). The presence of destabilizing contributions caused by the dehydration is in most scoring functions not taken into account. Summing up of only the stabilizing contributions and neglecting the destabilizing contributions explains the observed correlation between the score and the molecular weight of a respective compound. This correlation is not observed in experimental data. In addition, most scoring functions require various other empirical terms which are obtained in many cases from calibrations using experimental binding data. As seen in example 3, the balance of the individual interaction types contributing to the binding is strongly dependent on the temperature and additives. Therefore, many calibrations of the intermolecular interaction types using experimental binding data may be severely flawed since data from different and often incompletely described experiments are used.

In present invention, the hydrophobic effect is for the first time quantitatively described as the Gibbs free dehydration energy of apolar functions. Thus, we propose to calculate the non-covalent contribution to intermolecular interactions in aqueous solution by considering the sum of two terms (a) the dehydration of the interacting molecular interfaces ($\Delta G_{dehydration}$), (b) the vacuum H-bonds energies between interacting H-bond functions ($\epsilon^{i \cdots j}$). In addition, the changes in the Gibbs free energy of molecule A and B upon binding ($\Delta G_A$ and $\Delta G_B$) have to be taken into account.

$$\Delta G_{bound/unbound} = \Delta G_{dehydration} + \sum_{\substack{i=1 \ldots n \\ j=1 \ldots n}} \epsilon^{i \cdots j} + \Delta G^A + \Delta G^B$$

i=1, ... n: atoms of molecule A located in interface
j=1, ... m: atoms in molecule B located in interface The Gibbs free energy of dehydration may be included either directly into the intermolecular interactions such as the H-bonds (I) or calculated independently and added to the contributions from the H-bonds (II).

(I) Including the Gibbs free energy of dehydration directly into the intermolecular contributions results in:

$$\Delta G_{bound/unbound} = \sum_{\substack{i=1 \ldots n \\ j=1 \ldots m}} \Delta G^{i,j} + \Delta G^A + \Delta G^B$$

$$\text{with } \Delta G^{i,j} = \Delta G^i_{Dehydration} + \Delta G^j_{Dehydration} + \sum_{\substack{i=1 \ldots n \\ j=1 \ldots n}} \epsilon^{i \cdots j}$$

$\Delta G^i_{Dehydration}$ Gibbs free energy of dehydration for atom i of molecule A $\Delta G^j_{Dehydration}$ Gibbs free dehydration energy for atom j of molecule B The $\Delta G^{i,j}$ are identical to the terms described in examples 1-3.

(II) Alternatively, it may be more straightforward and more intuitive to calculate the Gibbs free dehydration energy before the interactions terms are calculated since two independent processes which obey different physical principles are described. Thus $$\Delta G_{bound/unbound} = \Delta G_{dehydration} + \sum_{\substack{i=1 \ldots n \\ j=1 \ldots n}} \epsilon^{i \cdots j} + \Delta G^A + \Delta G^B$$

$$\text{with } \Delta G_{dehydration} = \sum_{i=1 \ldots n} \Delta G^i_{dehydration} + \sum_{j=1 \ldots m} \Delta G^j_{dehydration}$$

Many functional groups do not belong to the two extreme cases outlined above and fall into the category $\epsilon_0^{wat \cdots wat} \ll \epsilon_0^{function \cdots wat} < 0$ and/or are not accessible to water with ideal geometry. Thus, there was a need to determine an estimate for H-bond energies for all functional groups occurring in intermolecular interfaces. Similarly, their dehydration cannot be calculated exactly using the terms for ideal functions and alternative methods are needed in order to estimate either the Gibbs free dehydration energy of the functional groups. If either the Gibbs free dehydration energy of a functional group or its H-bond energy to water is available, the following term can be used in order to calculate the missing value:

$$\Delta G_{dehydration}^i \sim f_{sat}^{i \cdots wat}$$

H-bond energies can be either estimated using experimental approaches such as Raman spectroscopy and IR spectroscopy. Alternatively, it is possible to calculate H-bond energies for instance using quantum mechanical methods. The calculation of the Gibbs free dehydration energy can be done using different approaches considering either the whole molecule or using an incremental approach. This includes the use of geometrical calculations in analogy to Eisenberg and MacLachlan (Nature 1986, 319: 199-203), free energy analyses based on force fields (Radmer and Kollman, J. Comp.-Aided Mol. Des. 1998, 12: 215-227) and the calculation of the chemical potential in aqueous solution. Approximate dehydration free enthalpies may be derived from molecular dynamics (MD) or Monte Carlo (MC) simulations which take all interacting moieties, i.e. both molecules and solvent, explicitly into account. Another approach to approximate dehydration free enthalpies is provided by the program COSMO-RS theory which describes the interactions in a solvent as local contact interactions of molecular surfaces (Klamt et al., J. Comp.-Aided Mol. Des. 2001, 15: 355-365). The problem of interacting molecules is reduced to pairs of interacting surfaces characterized by so-called σ-profiles which can be calculated by quantum mechanical methods. For the calculation of free energy-related entities, the least demanding approaches in terms of computational effort are incremental methods. For instance, c log P (BioByte Inc., California, USA) and A log P (Ghose and Crippen, J. Comp. Chem. 1988, 9: 80-90) are well-established methods to calculate octanol-water partition coefficients (log P) which represent the difference in free solvation energies in water and octanol. C log P is based upon the recognition of molecular fragments within a molecule and summation of their group contributions to the partition coefficient while A log P adds up contributions related to the individual atom types present in a particular molecule.

In our approach, the atom type contributions (i.e. the increments) were determined via a regression using a representative set of molecules with experimentally known log P values. The log P value of a compound is the decadic logarithm of its partition coefficient $K_{octanol/water}$ between n-octanol and water. Assuming that the Gibbs free dehydration energy of a molecule is small in octanol compared to that in water, the log P value can be also used as a measure of the Gibbs free dehydration energy of a given molecule:

$$\Delta G_{dehydration} \approx RT \ln K = -2.3 RT \cdot \log P$$

An expansion of the incremental approach is a surface-weighted contribution model. The group or atomic contributions are multiplied by the solvent accessible surface (SAS) of the corresponding groups or atoms before they are added. Eisenberg et al. successfully applied such a method to estimate stabilities of protein structures in water (Eisenberg Nature 1986, 319: 199-203). Wang et al. (J. Phys. Chem. B 2001, 105: 5055-5067) demonstrated the superior outcome in log P prediction by incorporating the SAS into the increment parameterization.

In our approach, we derived quasi-experimental Gibbs free dehydration enthalpies based on the above mentioned log P approximation. A set of 69 so-called geometry types was defined representing the various atom types in their particular chemical and geometrical environment. A geometry type was assigned to all non-hydrogen atoms of each of the molecules in the data set and a vector for each molecule was generated containing either the occurrences or the solvent accessible surface (SAS) of each of the geometry types. The calculated log P of a molecule using an occurrence based model is:

$$\log P^A = \sum_{k=1}^{n} occ_k^A \cdot p\log P_k^{occ}$$

Here, $occ_k^A$ is the occurrence of geometry type k in molecule A and $p \log P_k^{occ}$ is its increment which can be determined by solving the system of linear equations by multi-linear regression. For a surface-weighted model, the molecular vector contains a solvent accessibility dependent value $f_{acc,k}$ of the corresponding geometry types instead of their occurrence. The calculated log P is then:

$$\log P^A = \sum_{k=1}^{n} f_{acc,k}^A \cdot p\log P_k^{acc}$$

$f_{acc,k}^A$ depends on the accessibilities $acc_k$ of all atoms of geometry type k in molecule A. The derived $p \log P_k^{acc}$ therefore is dependent not only on the occurrence of an atom type but on its accessibility to the solvent as well. The accessibility value can be calculated as the sum over all atoms i of geometry type k in molecule A:

$$f_{acc,k}^A = \sum_i \frac{wsas_i}{wsas_{k,mean}} \; i: \text{atoms of geometry type } k \text{ in molecule } A$$

Here, $wsas_i$ is the weighted solvent accessible surface area of atom i and $wsas_{k,mean}$ is the mean accessibility of geometry type k in the parameterization dataset. $wsas_i$ is calculated according to Lee and Richards (J. Mol. Biol. 1971, 55: 379-400). In addition, the SAS algorithm was modified such that it takes directional effects of polar function into account. The surface regions which would make good H-bonds to water contribute more strongly to wsas compared to those which do not form good H-bond to water (e.g. perpendicular to the amide binding plane).

Thus, the Gibbs free dehydration energy of molecule A can be calculated as $$\Delta G_{dehydration}^A \approx -2.3RT \cdot \sum_{k=1}^{n} f_{k,acc}^A \cdot p\log P_k^{acc}$$

A dataset consisting of 696 molecules with measured log P was used (Hansch et al., 1995). Multi-linear regression was performed to determine the increments $p \log P_k^{acc}$ for the 69 different geometry types. Reasonable correlation coefficients of around 0.8 could be achieved. The description of the geometry types, their incremental $p \log P_k^{acc}$ values and the maximal Gibbs free dehydration energy for each geometry type are listed in Table 1.

TABLE 1

Geometry types and their respective plogP

| ID | plogP | Acc | ID | plogP | Acc |
|---|---|---|---|---|---|
| Hydrogen | 0.00 | 0.00 | C_sp_dd_H0 | 0.00 | 0.27 |
| C_sp_st_H0 | 0.00 | 0.18 | C_sp2_ggg_H0 | 0.10 | 0.10 |
| C_sp_st_H1 | 0.18 | 0.63 | Metal | −2.00 | 1.00 |
| C_sp2_aaa_H0 | 0.10 | 0.03 | N_sp_st_H0 | 0.00 | 0.17 |
| C_sp2_saa_H0 | 0.00 | 0.02 | N_sp_st_H1 | −0.84 | 0.10 |

TABLE 1-continued

Geometry types and their respective plogP

| ID | plogP | Acc | ID | plogP | Acc |
|---|---|---|---|---|---|
| C_sp2_saa_H1 | 0.43 | 0.26 | N_sp2_sd_H0 | −1.05 | 0.06 |
| C_sp2_ssd_H0 | 0.00 | 0.02 | N_sp2_sd_H1 | −1.05 | 0.24 |
| C_sp2_ssd_H1 | 0.34 | 0.23 | N_sp2_ss_H0 | −1.15 | 0.04 |
| C_sp2_ssd_H2 | 0.77 | 0.56 | N_sp2_ss_H1 | −0.95 | 0.24 |
| C_sp3_ssss_H0 | 0.00 | 0.00 | N_sp2_ssd_H0 | 0.00 | 0.00 |
| C_sp3_ssss_H1 | 0.12 | 0.08 | N_sp2_ssd_H1 | −1.05 | 0.06 |
| C_sp3_ssss_H2 | 0.48 | 0.24 | N_sp2_ssd_H2 | −1.05 | 0.15 |
| C_sp3_ssss_H3 | 0.74 | 0.54 | N_sp2_ssg_H0 | 0.00 | 0.02 |
| Fluorine | 0.30 | 0.36 | N_sp2_ssg_H1 | −1.15 | 0.05 |
| Chlorine | 0.56 | 0.40 | N_sp2_ssg_H2 | −0.94 | 0.13 |
| Bromine | 0.68 | 0.58 | N_sp2_ssm_H0 | 0.00 | 0.00 |
| Iodine | 0.90 | 0.65 | N_sp2_ssm_H1 | −1.15 | 0.04 |
| N_sp_t_H0 | −0.84 | 0.55 | N_sp2_ssm_H2 | −0.94 | 0.16 |
| N_sp2_aa_H0 | −1.05 | 0.08 | N_sp3_ssss_H0 | 0.00 | 0.00 |
| N_sp2_saa_H0 | 0.00 | 0.04 | N_sp3_ssss_H1 | −1.43 | 0.01 |
| N_sp2_saa_H1 | −0.55 | 0.09 | N_sp3_ssss_H2 | −1.72 | 0.10 |
| N_sp2_snn_H0 | 0.00 | 0.11 | N_sp3_ssss_H3 | −1.31 | 0.21 |
| N_sp2_sss_H0 | 0.00 | 0.00 | O_sp2_a_H0 | −0.97 | 0.27 |
| N_sp2_sss_H1 | −1.15 | 0.06 | O_sp2_saa_H0 | 0.00 | 0.00 |
| N_sp2_sss_H2 | −0.94 | 0.15 | O_sp2_saa_H1 | −0.54 | 0.11 |
| N_sp3_sss_H0 | −1.43 | 0.03 | O_sp3_s_H0 | −1.13 | 0.37 |
| N_sp3_sss_H1 | −1.72 | 0.10 | Phosphorus | 0.00 | 0.00 |
| N_sp3_sss_H2 | −1.31 | 0.22 | S_sp2_d_H0 | 0.00 | 0.60 |
| O_sp2_aa_H0 | −0.63 | 0.14 | S_sp3_ss_H0 | 0.00 | 0.42 |
| O_sp2_d_H0 | −0.80 | 0.17 | S_sp3_ss_H1 | 0.00 | 0.64 |
| O_sp2_n_H0 | 0.00 | 0.38 | Silicon | 0.00 | 0.00 |
| O_sp3_ss_H0_AA | −1.38 | 0.11 | Sulfur | 0.00 | 0.00 |
| O_sp3_ss_H0_Aa | −0.48 | 0.11 | | | |
| O_sp3_ss_H0_aa | 0.00 | 0.30 | | | |
| O_sp3_ss_H1 | −1.13 | 0.21 | | | |
| O_sp3_ss_H2 | −1.38 | 0.36 | | | |

As expected, the increments for polar geometry types such as carbonyls or hydroxyl functions are negative while the increments for apolar geometry types such as carbons are positive in their algebraic sign.

The surface-weighted contribution model has the additional advantage that the algorithm providing the solvent accessible surface area of the atoms can directly be used to calculate the dehydration energy of an interface. The latter represents those parts of the surface area which where previously solvent accessible but which are no no longer accessible after the molecular interface is formed. Thus, the Gibbs free dehydration energy of atom i of molecule A in the interface is:

$$\Delta G_{dehydration}^{A,i} = -2.3RT \Delta f_{acc}^i \cdot p \log P_i^{acc}$$

$\Delta f_{acc}$ is the difference in the accessibility of atom i between the bound and the unbound state. $p \log P_i^{acc}$ is the partial dehydration increment according to the geometry type of atom i.

To make the approach consistent, the calculation of the H-bond energy can be done using the relationship between the H-bond energy and the Gibbs free dehydration energy for an ideal polar function. According to present invention, the Gibbs free dehydration energy for polar molecules is reduced by the factor $f_{sat}$. Thus, in order to estimate the contribution towards a H-bond for a functional group the Gibbs free dehydration energy for this function has to be divided by $f_{sat}$ and can be calculated as:

$$\Delta G_{H-bond}^i = 1/f_{sat} \cdot 2.3RT \cdot \Delta f_{ia}^i \cdot p \log P^i$$

Here, $\Delta f_{ia}$ describes the changes in the interacting surface and equals 1 if it is reasonable large indicating that the H-bond has a reasonable good geometry. The H-bond energy between any atom i and any atom j can be calculated as the sum of their individual contributions towards the H-bond energy:

$$\Delta G_{H\text{-}bond}{}^{ij} = e^{polari} \cdots polarj = 1/f_{sat} \cdot 2.3RT \cdot (\Delta f_{ia}{}^i \cdot p \log P^i + \Delta f_{jd}{}^j \cdot p \log P^j)$$

The calculated score using the term in example 5 and which is part of this invention is called HYDE. All the relationships according to present invention and as described above can easily be implemented into standard computer programs describing the interaction between individual atoms.

Evidence 5a: Comparison of Calculated Contributions with Experimental Data

The agreement between the predicted intermolecular contributions such as interfacial H-bonds with the known experimental data is paramount for a good prediction. FIG. 8 shows a comparison between (a) the contributions obtained for the 'ideal functions' according to examples 1-3, (b) the corresponding contributions extracted according to example 5 and (c) the known experimental data (Eisenberg et al., Nature 1986, 319: 199-203; Reynolds et al., Proc. Natl. Acad. Sci. U.S.A. 1974, 71: 2925-7; Jeffrey, An Introduction to Hydrogen Bonding 1997, Publisher: Oxford Univ Press, Oxford; Fersht et al. Nature 1985, 314: 235-8; Savage et al. J. Chem. Soc. Faraday Trans. 1993, 89: 2609-17; Lange et al., J. Med. Chem. 2002, 45: 2915-22). The diagram shows that there is an excellent agreement (a) between the predicted contributions or our estimated values and (b) the experimental data. This is in stark contrast to the other scoring functions which are available to the public.

Evidence 5b: Predicting the Influence of a Single Atom in the Intermolecular Interface on $\Delta G_{bound/unbound}$ It has been observed, that a single atom exchange within an intermolecular interface has a dramatic effect on $\Delta G_{bound/unbound}$ (see Evidence 3a). This can be readily understood if one compares the contributions of individual atoms to $\Delta G_{bound/unbound}$. For instance, $\Delta G_{bound/unbound}$ of protein ligand complexes are often in the order of 10-30 kJ/mol and comprise in addition to the non covalent contribution described above, the changes of the Gibbs free energy of the protein and the ligand induced by ligand binding. The influence of a change in $\Delta G_{bound/unbound}$ on the affinity can be calculated using $\Delta G_{bound/unbound} = -RT \ln K$ (see Table 2).

TABLE 2

Differences in $\Delta G_{bound/unbound}$ and the corresponding changes in affinity

| $\Delta\Delta G_{bound/unbound}$ | change in affinity | $\Delta pK$ | affinity |
| --- | --- | --- | --- |
| 5.7 kJ/mol2 | factor $10^1$ | 1 | |
| 11.4 kJ/mol2 | factor $10^2$ | 2 | |
| 17.1 kJ/mol2 | factor $10^3$ | 3 | mM |
| 22.8 kJ/mol2 | factor $10^4$ | 4 | |
| 28.5 kJ/mol2 | factor $10^5$ | 5 | |
| 34.2 kJ/mol2 | factor $10^6$ | 6 | μM |
| 39.9 kJ/mol2 | factor $10^7$ | 7 | |
| 45.6 kJ/mol2 | factor $10^8$ | 8 | |
| 51.3 kJ/mol2 | factor $10^9$ | 9 | nM |
| 62.7 kJ/mol2 | factor $10^{10}$ | 10 | |
| 69.4 kJ/mol2 | factor $10^{11}$ | 11 | |
| 74.1 kJ/mol2 | factor $10^{12}$ | 12 | pM |

Figure 9A:
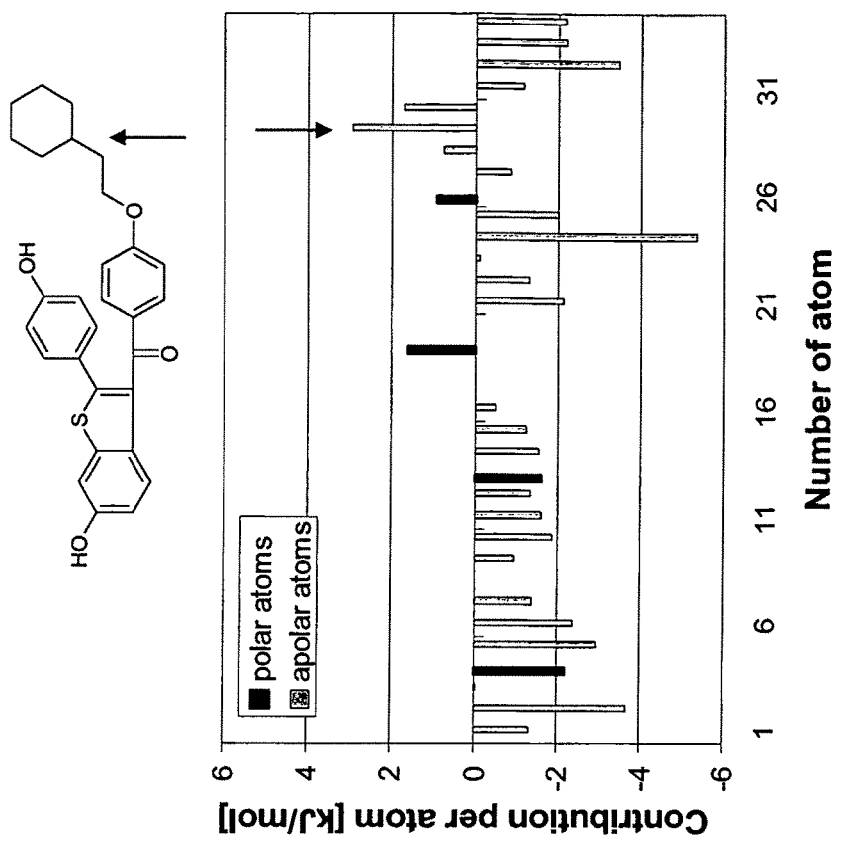
FIG. 9 A shows the calculated contributions to $\Delta G_{bound/unbound}$ of individual ligand atoms in the protein ligand interface of the estrogen receptor and raloxifene calculated based on the published structure (Brzozowski et al., Nature 1997, 389:753-758).
Figure 9B:
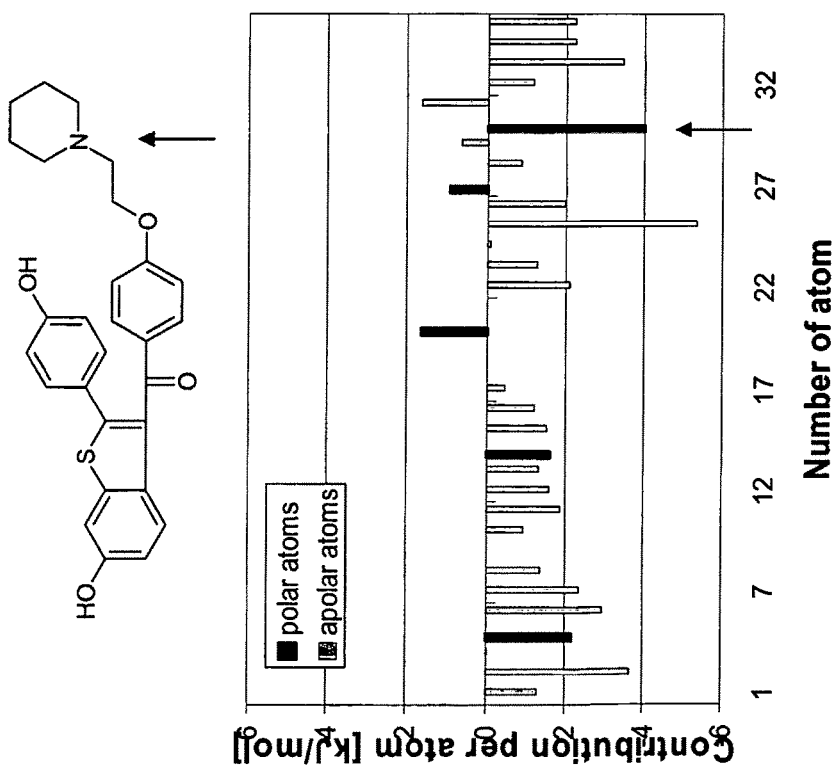
Figure 9:
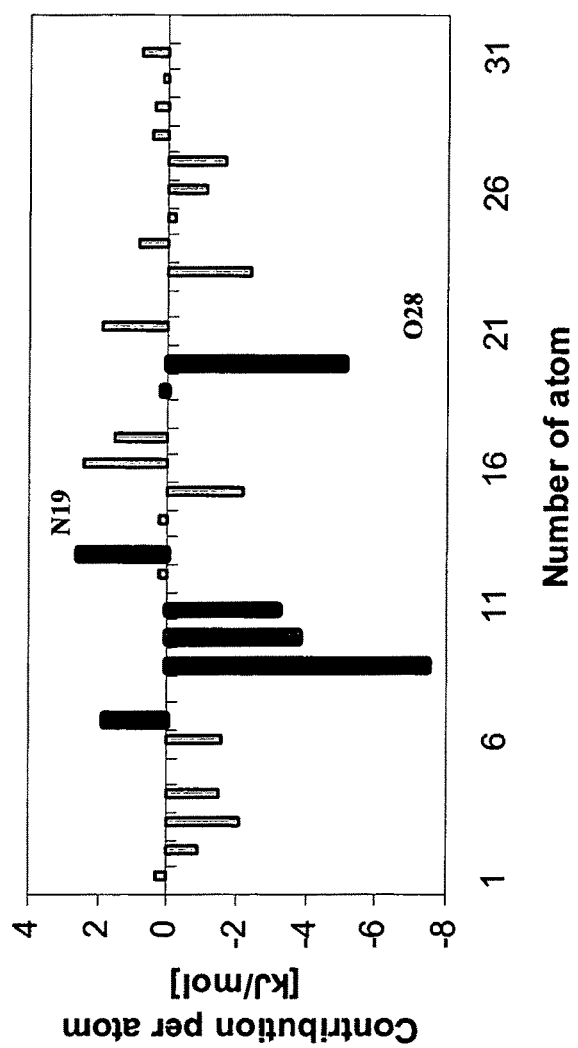

For instance a reduction in $\Delta G_{bound/unbound}$ of 11 kJ/mol corresponds to a 100 fold reduced affinity. An analysis of the individual contribution per atom shows that the contribution of many atoms is of a size which leads to a significant change in $\Delta G_{bound/unbound}$. In order to calculate the contribution of an individual ligand atom, the sum of its dehydration and its H-bonding contribution is calculated. The contributions of the receptor atoms are projected onto the ligand atoms according to the shared surface. FIG. 9 A shows the contribution towards $\Delta G_{bound/unbound}$ for each atom in the protein ligand interface of raloxifene (Brzozowski et al., Nature 1997, 389:753-758) bound to the Estrogen receptor. The size of the individual atomic contribution varies between −5.3 and 1.6 kJ/mol. Small changes within the interacting molecule lead to a significant altered affinity. For instance, replacing the nitrogen N29 with a carbon changes the contribution of this atom from −4.0 to +2.9 kJ. The change of 6.9 kJ corresponds to a 100 fold reduced change affinity (FIG. 9 B). Another example is the binding of Ru79181 (J. Med. Chem. 2002 45: 2915-22) to the SH2 domain of src. An analysis of the individual contributions per atom showed that the polar atom 028 contributes stabilizing to the protein ligand interface (−5.1 kJ/mol) since the H-bond which it forms to the protein has good geometry, while the polar atom N19 contributes destabilizing towards $\Delta G_{bound/unbound}$ (+2.6 kJ/mol) since the H-bond which it forms to the protein has a very bad geometry. As a result, Ru79181 (J. Med. Chem. 2002 45: 2915-22) binds surprisingly weak to the SH2 domain of src. The sign and the size of the contribution towards $\Delta G_{bound/unbound}$ can also be visualized for instance color coded in the 3-D representation of the protein ligand interface. Thus, the method according to present invention allows an analysis if a particular atom in an experimental or a calculated molecular interface contributes either favorably or unfavorably to $\Delta G_{bound/unbound}$ and also what type of changes are needed in order to improve the affinity between molecules.

Evidence 5d: Enrichment Plots

Figure 10:
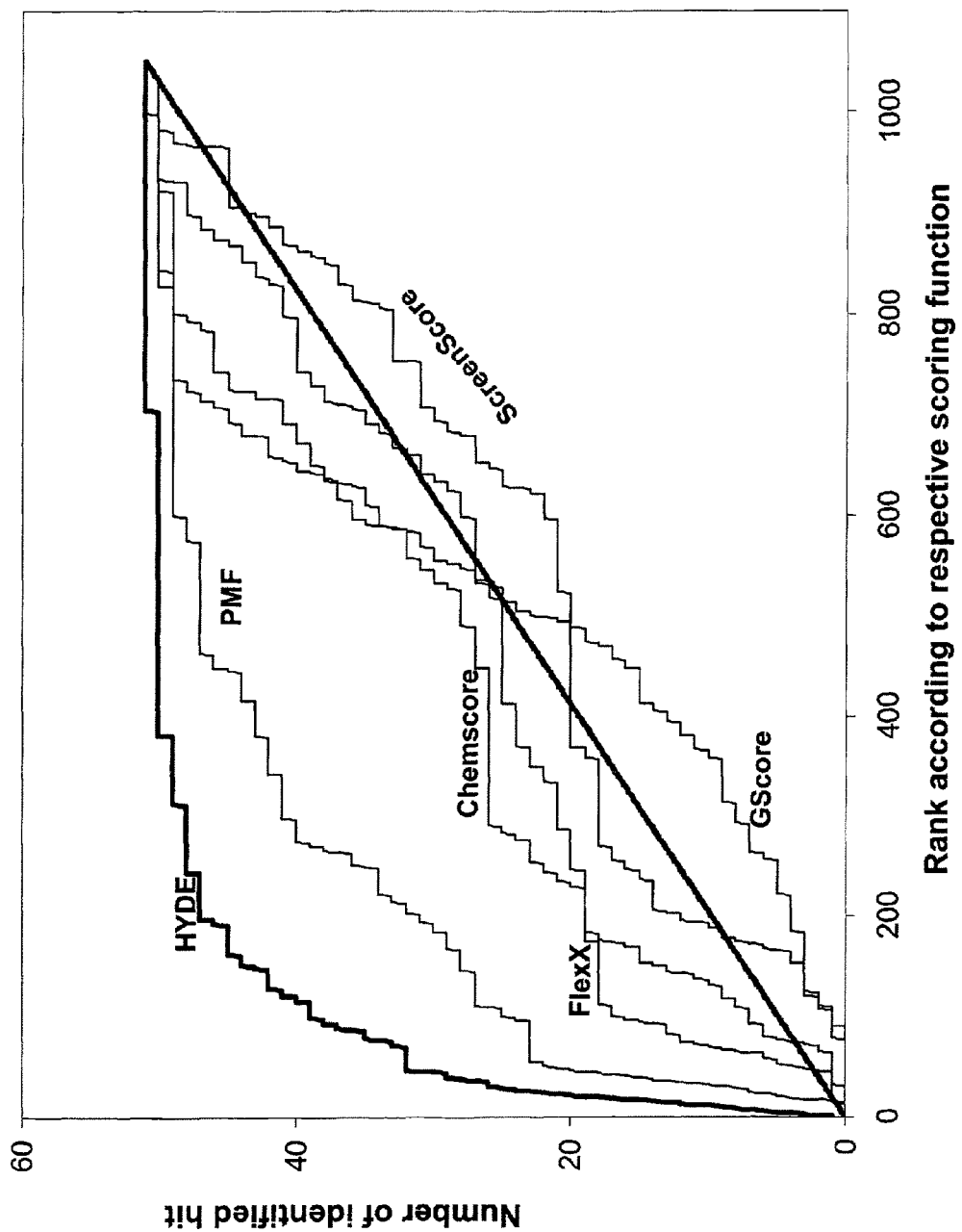
FIG. 10 A shows the enrichment calculations for Acc. The enrichment is shown for the following scoring functions: FlexX2.0, HYDE, ChemScore, G-Score, PMF-Score and ScreenScore.
Figure 10:
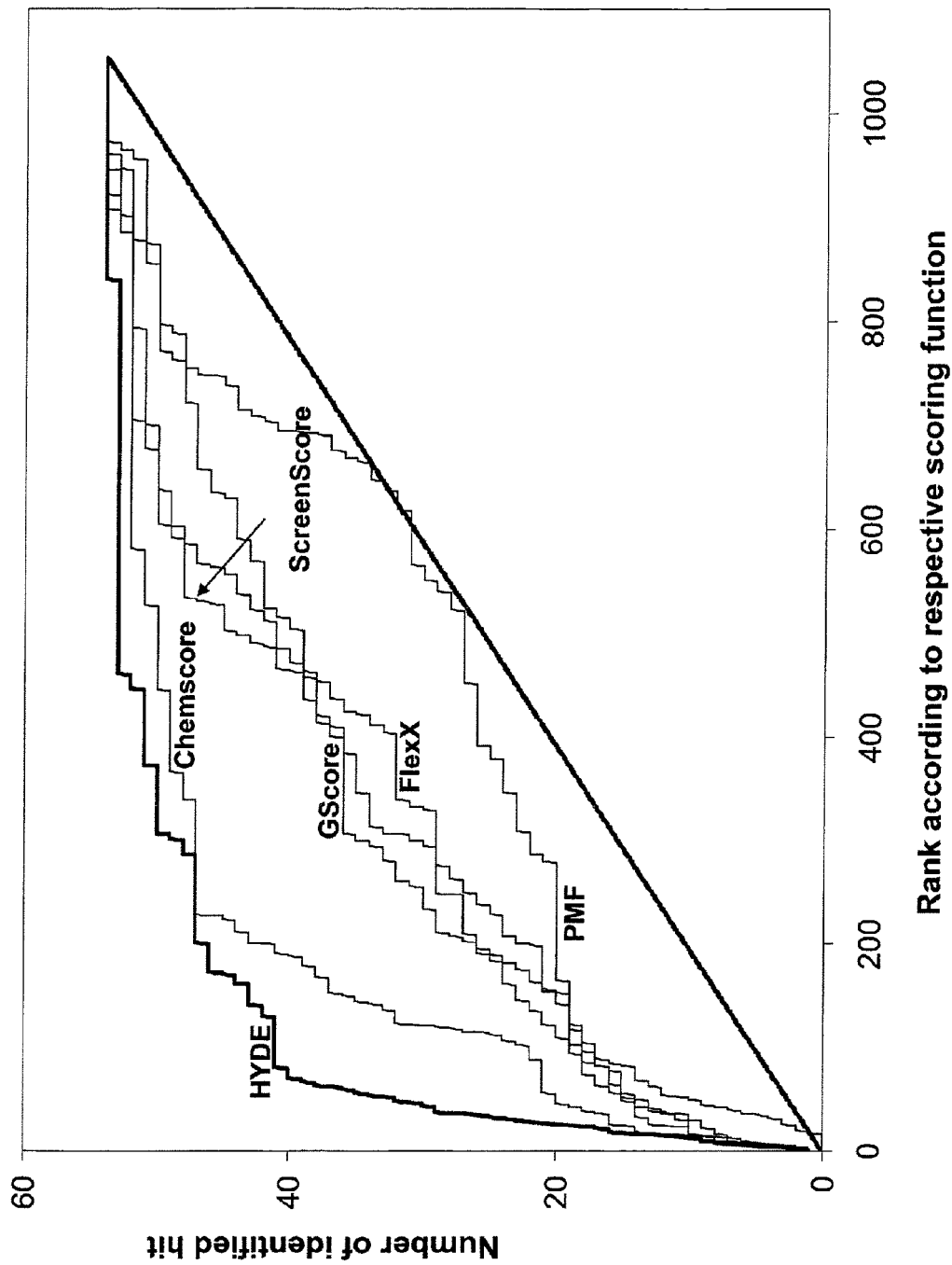
Figure 10:
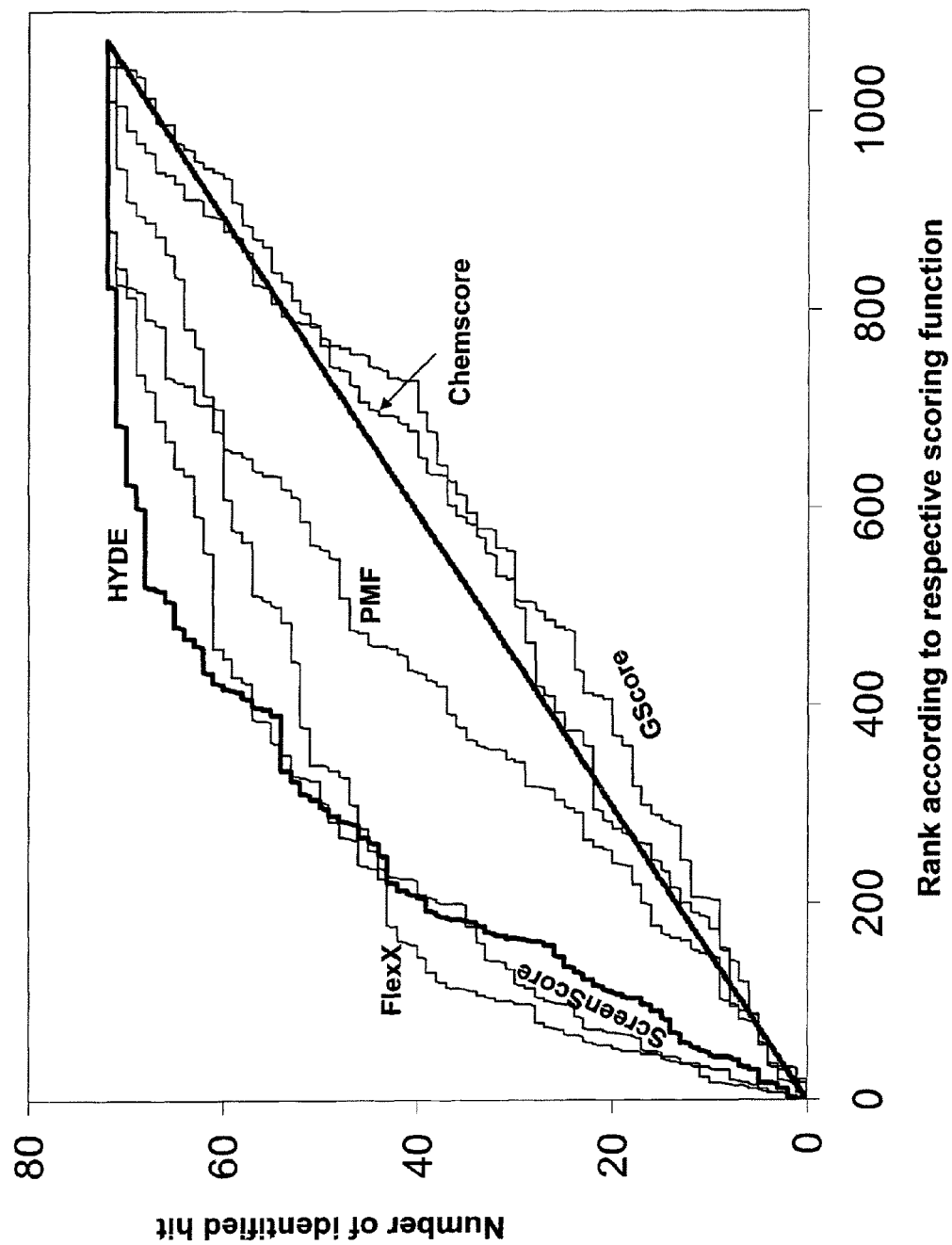
Figure 10:
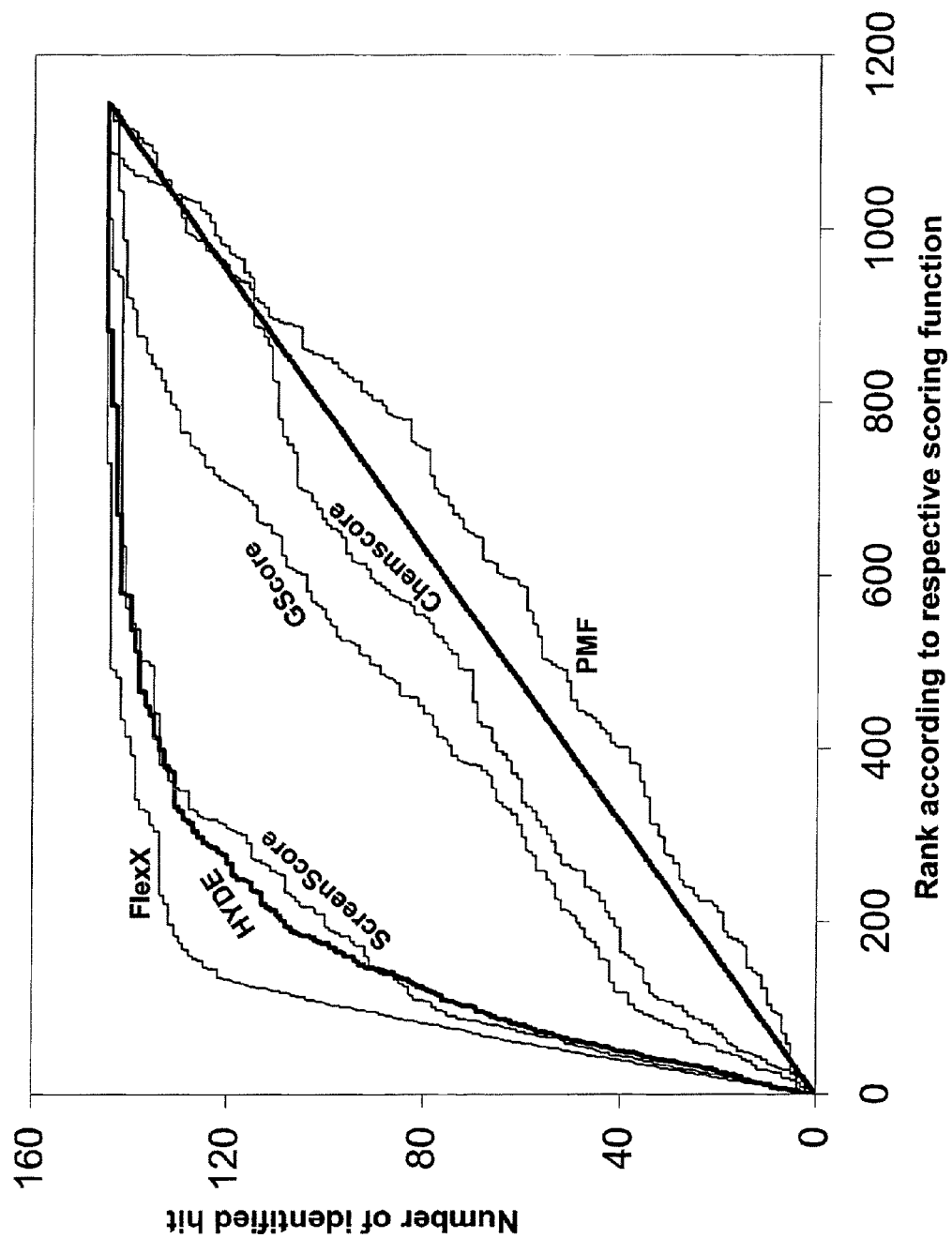

Scoring functions are often used to estimate the affinity between molecules in aqueous solutions in a high-throughput manner whereby the fit of thousands of molecules to a molecular target is calculated (virtual screening). In the case of ligands binding to protein molecules, the quality of a scoring function is often demonstrated in so called enrichment plots. Molecules of a library consisting of compounds with proven affinity to the investigated protein ('hits') and compounds which do not bind to that protein ('Random') are scored using this scoring function and ranked according to their score. The plot of the rank versus the sum of the identified hits up to this rank is shown in the enrichment plots. The enrichments calculated using different scoring functions are shown in FIG. 10 for four different targets which include (A) ACCase (proprietary crystal structure), (B) Estrogen receptor (identifier 1err from Protein data bank, Berman et al., Nucleic Acids Research 2000, 28: 235-242), (C) CDK2 (identifier 1di8 from protein data bank Berman et al., Nucleic Acids Research 2000, 28: 235-242) and (D) thrombin (identifier 1k22 from protein data bank, Berman et al., Nucleic Acids Research 2000, 28: 235-242). The scoring functions include (a) HYDE, (b) FlexX2.0 (c) Chemscore, (d) GScore, (e) PMF and (f) ScreenScore (program suite Sybyl 7.2, commercially available from Tripos Ltd. St. Louis). In case of ACCase 51 hits were added to a random set of 1000 compounds, in case of the estrogen receptor 53 hits, in case of CDK2, 72 hits and in case of thrombin 144 hits. All structures were prepared according to the requirements of FlexX2.0. FlexX2.0 was used in order to generate the poses i.e. the conformation in which the compound may bind to the protein. The best 50 poses were stored for all compounds and scored with the respective scoring function. Looking at FIG. 10 it becomes clear, that HYDE is the only scoring function which gives a reasonable enrichment for all four targets. All other scoring functions give rise to good enrichments for some targets but very poor enrichments for at least one other target. FlexX2.0, for instance gives rise to a very good enrichment in case of thrombin, while the enrichments in case of CDK2 and ACCase is poor. Similarly, Chemscore performs very well for the estrogen receptor but only poorly for ACCase, CDK2 and thrombin while PMF performs well for ACCase and poorly for the other targets. ScreenScore performs poorly for ACCase while GScore performs poorly in all four cases.

Evidence 5e: Selection of Hits from Library

Figure 11:
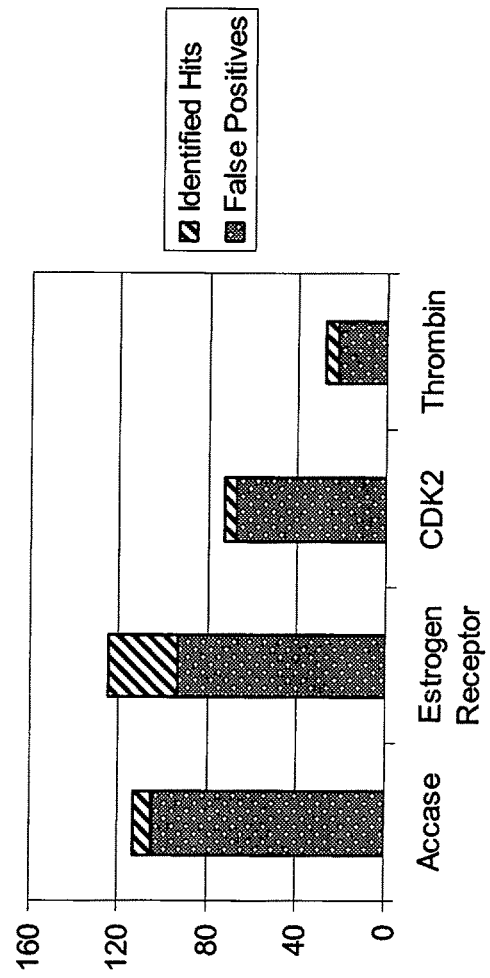
FIG. 11A shows the number of identified hits and false positives with a HYDE score better than −25 kJ/mol for the four targets accase, estrogen receptor, CDK2 and Thrombin.
FIG. 11B shows the number of identified hits with a score above −25 kJ/mol and the number of those compounds which are hits but were not identified (false negatives).
FIG. 11C shows the number of identified hits and false positives for the top scored compounds using FlexX2.0 and the same number of compounds as found for the HYDE score
FIG. 11D shows the number of identified hits and the number of those compounds which are hits but were not identified (false negatives) using FlexX2.0 and the same number of compounds as those found for the HYDE score.
FIG. 11E shows the number of identified hits and false positives for the top scored compounds using Chemscore and the same number of compounds as found for the HYDE score
FIG. 11F shows the number of identified hits and the number of those compounds which are hits but were not identified (false negatives) using Chemscore and the same number of compounds as those found for the HYDE score.
FIG. 11G shows the number of identified hits and false positives for the top scored compounds using Gscore and the same number of compounds as found for the HYDE score
FIG. 11H shows the number of identified hits and the number of those compounds which are hits but were not identified (false negatives) using Gscore and the same number of compounds as those found for the HYDE score.
FIG. 11I shows the number of identified hits and false positives for the top scored compounds using PMF-Score and the same number of compounds as found for the HYDE score
FIG. 11J shows the number of identified hits and the number of those compounds which are hits but were not identified (false negatives) using PMF Score and the same number of compounds as those found for the HYDE score.
FIG. 11K shows the number of identified hits and false positives for the top scored compounds using ScreenScore and the same number of compounds as found for the HYDE score
FIG. 11L shows the number of identified hits and the number of those compounds which are hits but were not identified (false negatives) using ScreenScore and the same number of compounds as those found for the HYDE score.
Figure 11:
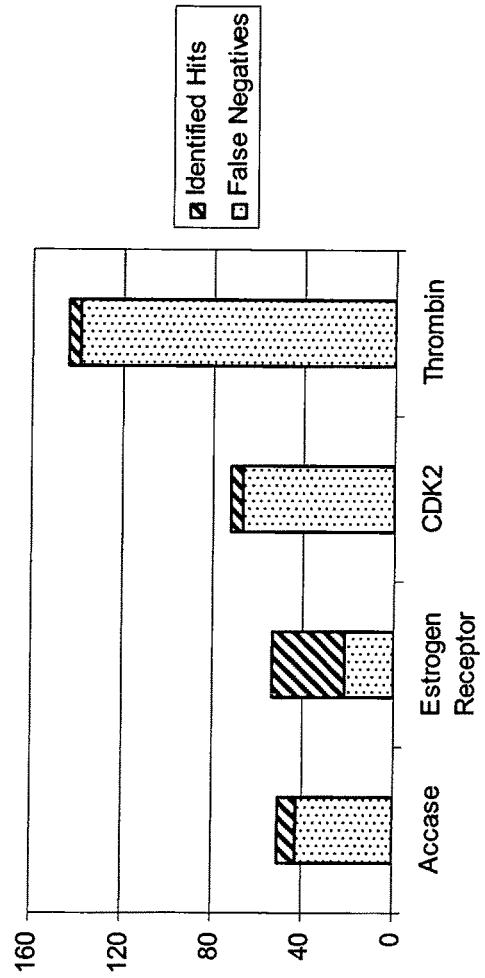
Figure 11:
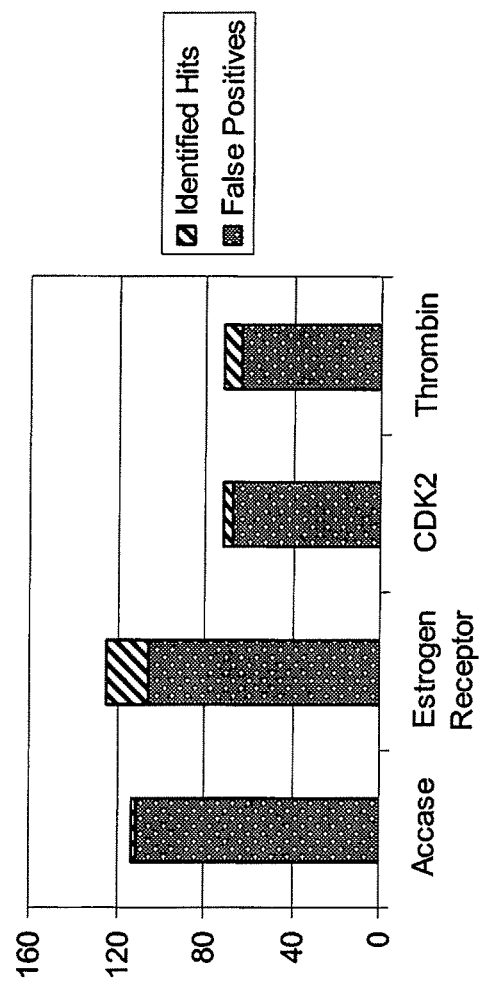
Figure 11:
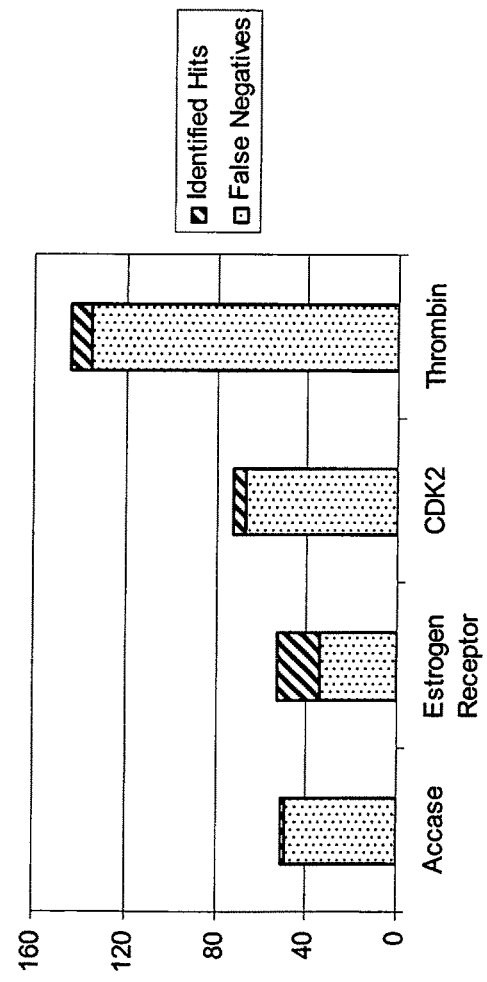
Figure 11:
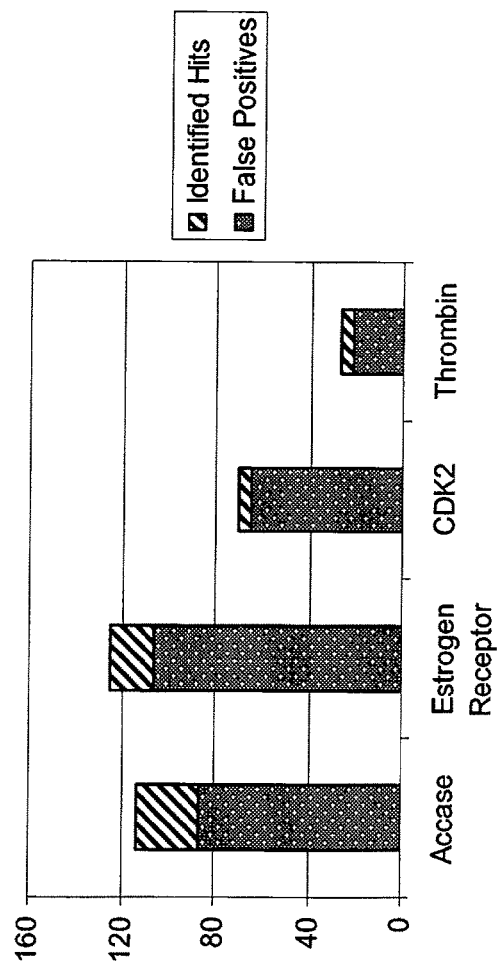
Figure 11:
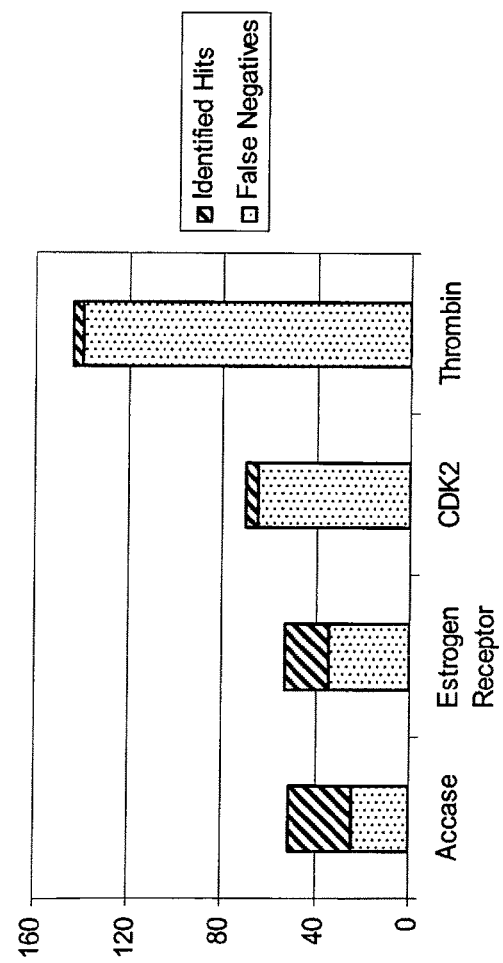
Figure 11:
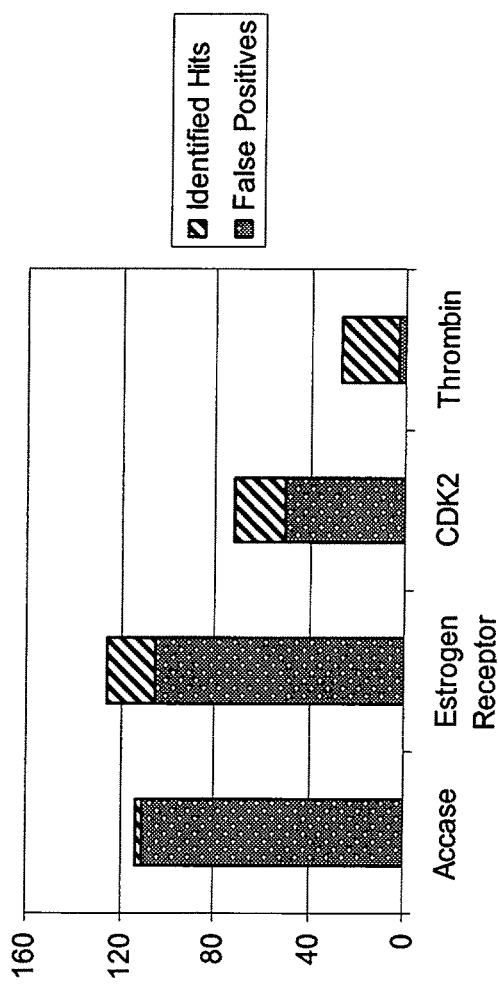
Figure 11:
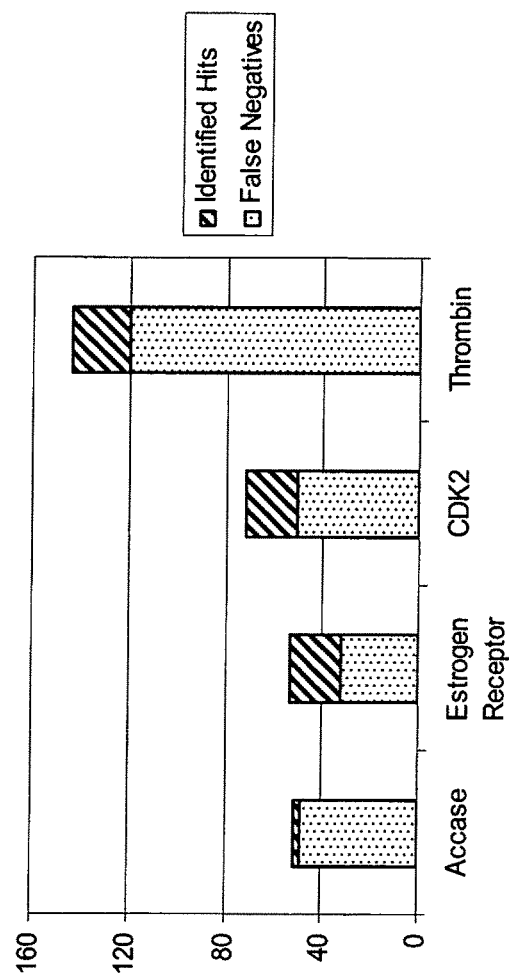

The purpose of virtual screening is the identification of compounds which bind to the target protein from compound libraries which may consist of up to several million molecules. In order to achieve that, the compounds are docked into the target protein and scored using a scoring function. The likelihood that a chosen molecule selected using a particular scoring function is indeed binding to the target protein reflects the quality of that scoring function. For most of the publicly available scoring functions there exists no general value which can be used as general cutoff score if a ligand binds to the protein or not. Instead, this cut-off score has to be defined for each protein individually. In many cases this cut-off score is defined based on criteria which include that a certain percentage of the 'hits' are identified up to this cutoff score. However, docking not always produces the correct pose. This may be caused by the pose generator (see for instance Evidence 5f) or by protein flexibility which is usually not accounted for. As a consequence, hits which may have a very good score if calculated using the correct pose, may have a very bad score and ranked very low. Thus, criteria which are based on including a certain percentage of 'hits' up to that cutoff score may lead to a significantly increased cutoff score and thus to a dilution of 'hits' within the considered scoring range. In our case, there is a minimum score which should be achieved if a molecule is considered to bind. This limit of −20 kJ/mol corresponds to an affinity of $10^4$M assuming that there is no change in Gibbs free energy of the ligand and the protein upon forming the complex. Alternatively, a more stringent upper limit −25 kJ/mol corresponding to an affinity of roughly $10^{-6}$M can be used. Using the cutoff value −25 kJ/mol, we calculated the number of 'hits' and false positive for the four different targets. Looking at FIG. 11A it becomes clear that in all cases a significant probability exists that a ligand with a score better than −25 kJ/mol belongs to the group of 'hits'. The probability that a compound with a score better than −25 kJ/mol is indeed a 'hit' ranges from 19% in case of CDK2 to 74% in case of thrombin. Interestingly, not all 'hits' have a score better than the cutoff score. In particular, for CDK2 and thrombin, a significant number of 'hits' had only calculated poses which scored worse than −25 kJ/mol using the HYDE score (FIG. 11B). This may be very well due to the flexibility of the target protein or due to the fact that the 'correct' pose had been not generated by the program FlexX. A similar analysis was made using the other scoring functions. For a better comparison, we used the same number of ligands for each target protein which had been identified using the HYDE score since there is no general cutoff-score for any of the other scoring functions. As FIGS. 11C-L show, the percentage of 'hits' within the same number of top ranked compounds is significantly smaller in case of all the other scoring functions. In addition, the number of identified 'hits' within these top ranked compounds is in many cases quite small compared to the total number of 'hits' within the data set. Defining the cut-off score using a percentage of identified hits such as 50% would very much increase the number of compounds better than this cutoff score. Thereby the percentage of 'hits' would be significantly diluted and the probability that a ligand better than the cut-off score is indeed a 'hit would be significantly reduced.

Figure 12:
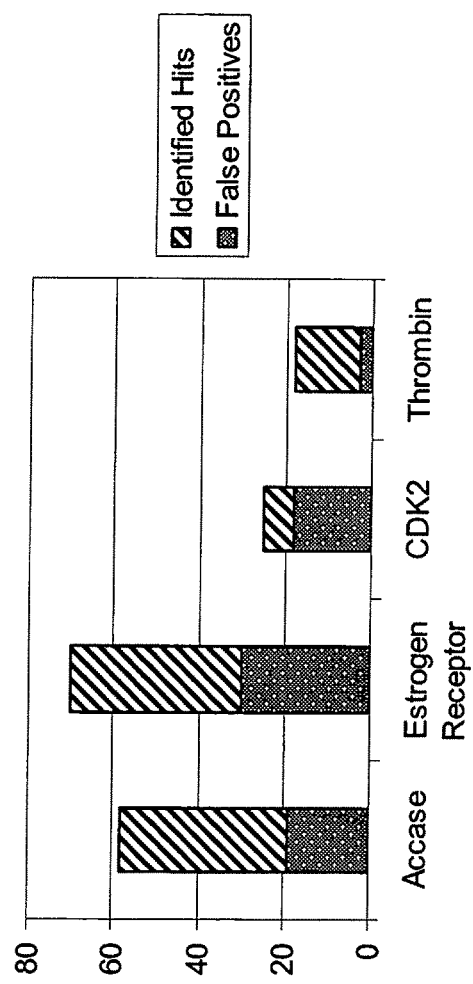
FIG. 12 shows the number of identified hits and false positives if the scoring function HYDE is used and additionally a filter for the internal conformational energy of 60 kJ/mol is applied.

In addition, further improvements are possible and include for instance a high conformational energy filter. Omitting all poses which have either a high internal conformational energy reduces the number of false positives even more. FIG. 12 shows the likelihood that a certain compound which binds to the respective protein according to HYDE and has an internal conformational energy with less than 60 kJ/mol is indeed a hit. The likelihood ranges from 88% in case of thrombin to 28% in case of CDK2.

Evidence 5f: Identification of Correct Binding Mode

Figure 13:
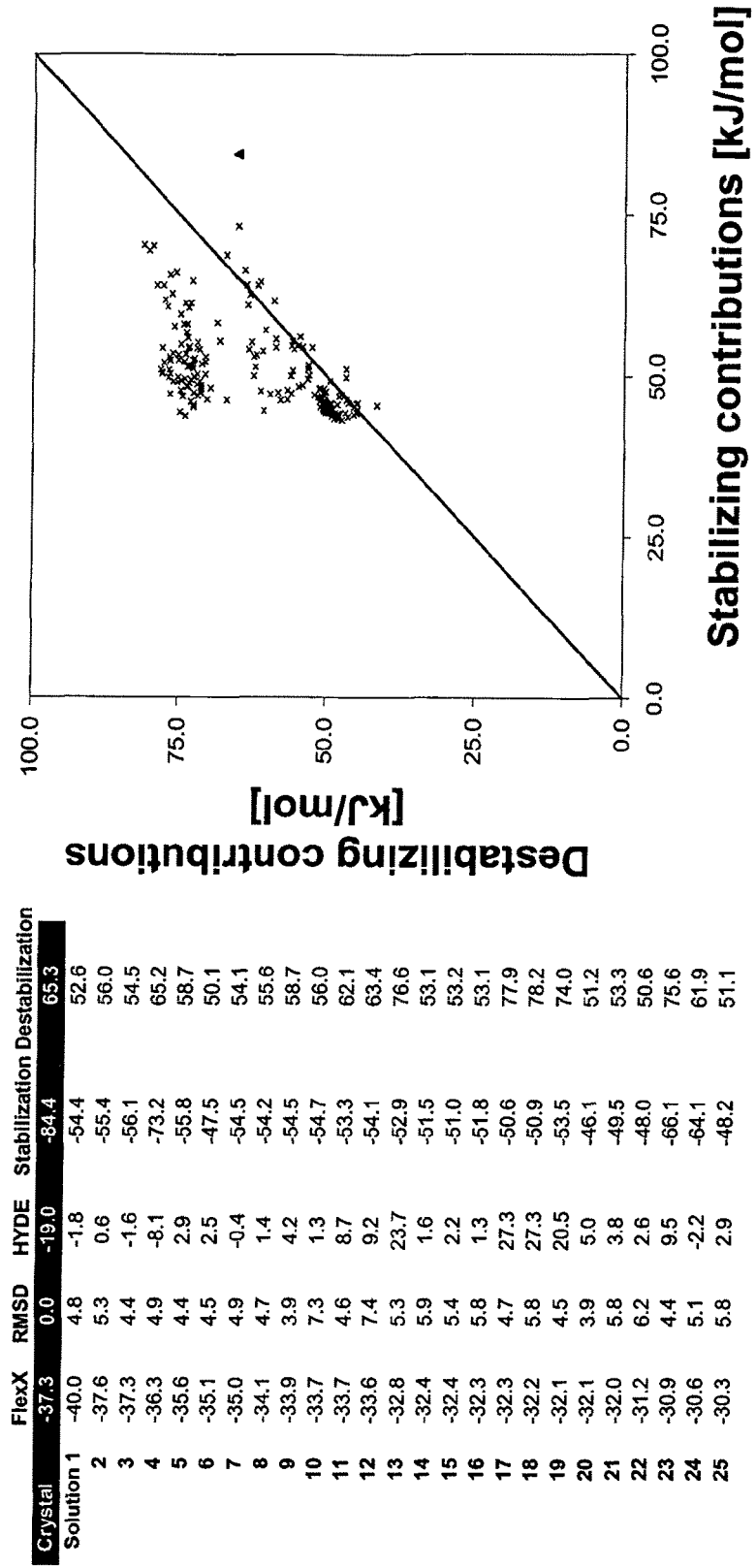
FIG. 13 A shows a table showing the FlexX2.0 score, the root mean square deviations between atomic positions in the crystal structure and the respective docked pose, the Hyde score and the stabilizing and destabilizing contributions calculated using our approach for the experimental crystal structure and the first 25 docking solution calculated using FlexX2.0.

It is important that scoring functions can distinguish between correct and wrong binding geometry within the intermolecular interface (poses). Otherwise no further analysis is possible and no ultimate statement can be made as to whether a particular compound binds to the target protein or not. In addition, it is a good sign of overall compatibility if correct poses are scored highly while wrong poses have an unfavorable score. As example, the binding of RU79181 (J. Med. Chem. 2002 45: 2915-22) to the SH2 domain of src will be used here. FIG. 13 A shows the FlexX2.0 and the HYDE score for the pose observed in the experimental x-ray structure and the docking poses which were generated using FlexX2.0. It becomes clear that the pose observed in the experiment is scored as 'binding' for both the FlexX2.0 and the HYDE score. In contrast, the docked poses are scored by FlexX2.0 as highly favorable while the same poses are scored by HYDE such that one can conclude that these docked poses will not be observed in the experiment. This is confirmed by a visual inspection of the poses. In addition, the root mean square deviations between the position of inhibitor atoms in the x-ray and the respective docked poses is rather high indicating that none of the docked poses superimposes reasonable well with the experimental structure. Thus, the prediction made by HYDE that none of the docked poses will be found in the experiment is correct, while FlexX2.0 scores the experimental structure correctly but generates many false positives which have a similar or even better score than the experimental structure. As described above, this results from neglecting the destabilizing contributions towards $\Delta G_{bound/unbound}$. FIG. 13 B shows the stabilizing versus the destabilizing contributions for the experimental structure and the first 25 docking solutions. Here, the stabilizing contribution consists of the sum of the H-bond contributions and the hydrophobic effect arising due to ligand binding while the destabilizing contributions consists of the Gibbs free dehydration energy of the polar atoms and of those apolar atoms pointing towards the aqueous solution. It becomes clear that only in case of the experimentally observed interface the stabilizing contributions outweigh the destabilizing contributions considerably while for all docking solutions the destabilizing contributions are similar or even larger than the stabilizing contributions indicating that none of the docking solution is correct. Thus, HYDE allows to distinguish between correct and wrong positioning of a ligand. This is required in order to determine which portion of the interacting molecule contributes favorably or unfavorably to $\Delta G_{bound/unbound}$.

The invention claimed is:

1. A method for binding together at least two molecules, at least one target and at least one interacting molecule, so as to obtain a molecular complex, in an aqueous solution wherein the at least one target molecule is in a first library and the at least one interacting molecule is in a second library, said method comprising the steps of
  (I) determining an interaction of each combination of a molecule from the first library and a molecule from the second library using a sufficiently programmed computer by the following steps:
    (a) determining a dehydration energy ($\Delta G_{dehydration}$) of all atoms in an intermolecular interface between the target molecule and at least one interacting molecule, wherein the atoms are selected from the group consisting of atoms with a polar function and atoms with an apolar function,
(b) adding a vacuum hydrogen bond energy ($\epsilon_H$-bond) between all atoms in the intermolecular interface to the determined dehydration energy so as to produce a result (a)+(b), and
(c) adding to the result (a)+(b) a change in the free enthalpy of the target molecule interacting with the at least one molecule upon their interaction so as to obtain possible molecular interactions,
(II) identifying at least one interacting molecule that is capable of binding to the target molecule from the possible molecular interactions and
(III) pairing the identified interacting molecule, so that the target molecule is bound to the identified interacting molecule so as to obtain a molecular complex.

2. The method according to claim 1, wherein for the atoms with a polar function the dehydration energy is calculated by the following formula:

$$\Delta G^{polar}_{dehydration} = -f_{sat} \cdot \varepsilon^0_{pol\ldots wat} + \frac{1}{2} f_{sat} \cdot \varepsilon^0_{wat\ldots wat}$$

wherein
$f_{sat}$ is the determined fraction of saturated H-bond functions within the water network,
$f_{unsat}$ is the determined fraction of unsaturated H-bond functions within the water network,
$\varepsilon^0_{wat\ldots wat}$ is the determined hydrogen bond energies between water molecules in the water network, and
$\varepsilon^0_{pol\ldots wat}$ is the determined hydrogen bond energy between the polar function and the water network.

3. The method according to claim 1, wherein for the atom with an apolar function the dehydration energy is calculated by the following formula:

$$\Delta G^{apolar}_{dehydration} = +\frac{1}{2} \cdot \varepsilon^0_{wat\ldots wat}\left(1 - \frac{T}{373K}\right) > 0,$$

wherein $\varepsilon^0_{wat\ldots wat}$ is the determined hydrogen bond energies between water molecules in the water network.

4. The method according to claim 2, wherein $f_{sat}$ and $f_{unsat}$ are defined in pure bulk water by the terms as listed under (a) and (b):

$f_{sat}(T) = (\Delta H_{Fusion} + c_p(T-273K)/(\Delta H_{Fusion} + \Delta H_{Evaporation} + c_p*(373K-273K))$, and  (a)

$f_{unsat}(T) = (\Delta H_{Evaporation} + c_p*(373K-T)/(\Delta H_{Fusion} + \Delta H_{Evaporation} + C_p*(373K-273K))$,  (b)

with the proviso that $f_{sat} + f_{unsat} = 1$,
and wherein
(i) $\Delta H_{Fusion}$ means the Enthalpy of the fusion of ice;
(ii) $\Delta H_{Evaporation}$ means the Enthalpy of Evaporation of water; and
(iii) $c_P$ means specific heat of water.

5. The method according to claim 2, wherein for the calculation of the dehydration energy an approximate equality exists as follows:

$\epsilon_{pol\ldots wat}^0 \approx \epsilon_{wat\ldots wat}^0$.

6. The method according to claim 2, wherein the dehydration energy for polar functions is represented by the following formula $$\Delta G^i_{dehydration} \approx \frac{1}{2} f_{sat} \cdot \varepsilon_{i\ldots wat}.$$

7. The method according to claim 2, wherein $f_{sat}$ is within a range 0.75 to 0.90.

8. The method according to claim 2, wherein $f_{sat}$ is within a range of 0.82 to 0.88.

9. The method according to claim 2, wherein $f_{sat}$ is within a range of 0.84 to 0.87.

10. The method according to claim 5, in which the target molecule in the first library is selected from the group consisting of proteins, nucleic acid molecules, and lipids.

11. The method according to claim 5, wherein the target molecule in the first library is selected from the group consisting of: cell wall proteins, membrane bound proteins, water soluble proteins, cellular proteins, enzymatic proteins, regulatory proteins, ion channel proteins, carrier proteins, aquaporins, vacuolar proteins, golgi apparatus proteins, cytoskeleton proteins, DNA- or RNA-replication proteins, DNA- or RNA-recombination proteins, viral proteins, mitochondrial proteins, plastid proteins involved in the respiration and photorespiration apparatus, proteins belonging to the signal transduction pathway, receptors, G-proteins, senescence proteins, plant stress proteins (including abiotic and biotic plant stress proteins), HMG-proteins (high mobility group proteins), LMG-proteins (low mobility group proteins), Terpenoid synthesis proteins, DNA-molecules, RNA-molecules, transcriptions factors, phospholipids, galactosylglycerides, glucocerebrosides, and sterols.

12. The method according to claim 5, in which the interacting molecule in the second library is selected from the group consisting of: proteins, enzyme inhibitors, agonists, antagonists, small weight compounds (molecular weight <600 g/mol) and fragments of the latter.

13. The method according to claim 1, in which the intermolecular interface between the target molecule and its interacting molecule is defined by three-dimensional coordinates that are:
(a) defined by experimental data obtained from protein crystallography methods, X-ray diffraction, or NMR, or
(b) obtained from computer based calculations by applying the means of docking, molecular dynamics (MD) or Monte Carlo (MC) simulations, or
(c) obtained by manual maneuvering of the interacting molecule inside its primary docking area of the target molecule.

14. The method according to claim 2, wherein for the calculation of the dehydration energy an approximate equality exists as follows $\epsilon_{pol\ldots wat}^0 \approx \epsilon_{wat\ldots wat}^0$.

15. The method according to claim 4, wherein the dehydration energy for polar functions is represented by the following formula $$\Delta G^i_{dehydration} \approx \frac{1}{2} f_{sat} \cdot \varepsilon_{i\ldots wat}.$$

16. The method according to claim 2, wherein the target molecule in the first library is selected from the group consisting of proteins, nucleic acid molecules, and lipids.

17. The method according to claim 2, wherein the interacting molecule in the second library is selected from the group consisting of: proteins, enzyme inhibitors, agonists, antagonists, small weight compounds (molecular weight <600 g/mol) and fragments of the latter.

* * * * *